United States Patent [19]

Matsukura et al.

[11] Patent Number: 5,541,213
[45] Date of Patent: Jul. 30, 1996

[54] PROPENOIC ACID DERIVATIVES DIAZOLE PROPENOIC ACID COMPOUNDS WHICH HAVE USEFUL PHARMACEUTICAL UTILITY

[75] Inventors: Masayuki Matsukura, Tsukuba; Keizoh Satoh, Ushiku; Naoki Yoneda; Makoto Kaino, both of Tsukuba; Kazutoshi Miyake, Ushiku; Yoshiharu Daiku, Tsuchiura; Naoya Kishi, Tsukuba; Fusayo Yoshida, Ushiku; Kenichi Nomoto, Tsukuba; Toshiaki Ogawa, Kitasouma; Tadanobu Takamura, Tsuchiura; Koichi Nose, Kitasouma-gun; Mikio Tomimatsu, Tsukuba; Masanori Mizuno, Kashima-gun; Shigeto Negi, Tsukuba; Shigeru Souda, Ushiku, all of Japan

[73] Assignee: Eisai Co., Ltd., Tokyo, Japan

[21] Appl. No.: 258,634

[22] Filed: Jun. 10, 1994

[30] Foreign Application Priority Data

Jun. 24, 1993 [JP] Japan ................... 5-177278
Jul. 23, 1993 [JP] Japan ................... 5-202903
Aug. 21, 1993 [JP] Japan ................... 5-227924
Aug. 31, 1993 [JP] Japan ................... 5-237188

[51] Int. Cl.$^6$ ................... C07D 401/14; C07D 231/10; C07D 233/54; A61K 31/415
[52] U.S. Cl. ................... 514/400; 514/333; 514/341; 514/406; 514/399; 514/397; 546/256; 546/14; 546/277.1; 546/266; 546/344; 546/264; 546/329; 546/262; 546/275.4; 546/275.1; 548/311.1; 548/312.4; 548/338.1; 548/338.5; 548/364.1; 548/375.1
[58] Field of Search ................... 546/256, 279, 546/283, 278; 548/375.1, 338.5, 311.1, 312.4, 364.1, 375.1, 338.1; 514/333, 341, 343, 406, 397, 399, 400

[56] References Cited

FOREIGN PATENT DOCUMENTS

| | | |
|---|---|---|
| 0225522 | 6/1987 | European Pat. Off. ............... 514/348 |
| 0278090 | 8/1988 | European Pat. Off. ............... 514/348 |
| 0299209 | 1/1989 | European Pat. Off. ............... 514/348 |
| 0497258 | 8/1992 | European Pat. Off. ............... 514/348 |
| 0516941A1 | 9/1992 | European Pat. Off. ............... 514/348 |

OTHER PUBLICATIONS

Chemical Abstracts, vol. 71, No. 13, Abstract 60.964t, Sep. 29, 1969, p. 402.

Chemical Abstracts, vol. 93, No. 7, Abstract 71,629t, Aug. 18, 1980, p. 965.

Chemical Abstracts, vol. 110, No. 25, Abstract 231, 632p, Jun. 19, 1989, p. 648.

Chemical Abstracts, vol. 111, No. 3, Abstract 23,508w, Jul. 17, 1989. pp. 617–618.

*Primary Examiner*—Zinna Northington Davis
*Attorney, Agent, or Firm*—Nixon & Vanderhye

[57] ABSTRACT

A novel propenoic acid derivative which exhibits adenosine A1 antagonism is defined by the general formula (I):

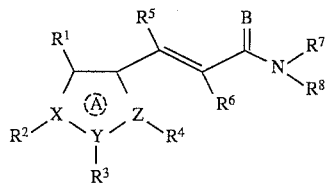

(wherein A represents an aromatic ring; $R^1$ represents aryl or the like; $R^2$, $R^3$ and $R^4$ each represent hydrogen, lower alkyl or the like; and $R^7$ and $R^8$ each represent lower alkyl or the like) or a pharmacologically acceptable salt thereof.

7 Claims, No Drawings

PROPENOIC ACID DERIVATIVES DIAZOLE PROPENOIC ACID COMPOUNDS WHICH HAVE USEFUL PHARMACEUTICAL UTILITY

FIELD OF INDUSTRIAL APPLICATION

The present invention relates to a propenoic acid derivative or a pharmacologically acceptable salt thereof which is useful as a drug. More particularly, it relates to a propenoic acid derivative or a pharmacologically acceptable salt thereof which exhibits adenosine antagonism.

BACKGROUND OF THE INVENTION AND PRIOR ART

A syndrome having oliguria, anuria, uremia and so forth as the main sign is called acute renal failure, which began to attract attention during the Second World War because it attacked people which had recovered from traumatic shock due to the air raid on London, and has come to the present state.

Although there are many causes of acute renal failure, it is believed that such failure is mainly caused by hemorrhage due to injury, surgical operation, aortic rupture or the like; diarrhea due to serious enteritis, infection with Salmonella or cholera, or the like; loss of water and/or electrolyte due to burn, continued vomiting, heat stroke or the like; hemolysis due to incompatible blood transfusion, hemoglobinuria or the like; angiopathy such as renal arterial thrombosis; infectious disease such as pneumonia, sepsis, acute hepatitis, pyelonephritis or candidiasis; allergy; anaphylaxis; influence of a carcinostatic agent such as cisplatin; urethral or ureteral obstruction due to prostatic hypertrophy or malignant tumor; urinary obstruction such as ureteral stone; or the like.

Further, a symptom of irreversible decrease in the number of nephrons is called chronic renal failure, and a patient with this failure cannot avoid dialysis with an advance in the symptom, suffering from physical and mental great agony. Additionally, the dialysis of a patient with chronic renal failure generally extends over a long period, so that his expense is also great. Further, it is apparent from the ratio of the number of dialyzers held in Japan to that of the patients necessitating dialysis that the dialyzers must now be worked without intermisission. Therefore, the fact that there are patients with serious acute renal failure who necessitate dialysis temporarily in addition to those with chronic renal failure is significantly problematic.

Under these circumstances, the prevention of the symptom of renal failure from reaching a stage necessitating dialysis has become a great issue. However, there has not been found as yet any means which is effective in the prevention of the symptom of chronic renal failure from reaching such a stage, while the regulation of the body fluid which has lost its balance owing to oliguria or anuria by the administration of a diuretic is conducted as the conservative therapy exclusively for the patients with acute renal failure to secure necessary thermal energy.

It has been a practice in the prior art to use a loop diuretic such as furosemide or ethacrynic acid against acute renal failure. However, such a diuretic causes an adverse reaction such as hearing loss, worsening of diabetes mellitus or hyperuricemia, so that enough care is needed in the administration thereof. Further, it is needless to say that these drugs are ineffective in protecting the kidney positively to normalize the lowered function thereof, because the drugs serve only as diuretic.

Accordingly, it has been expected eagerly to develop a drug which can prevent the worsening of renal failure and which can regulate the body fluid to thereby normalize the function of the kidney.

SUMMARY OF THE INVENTION

Under these circumstances, the inventors of the present invention have started their studies for the purpose of developing a remedy for renal failure.

As a result of the studies, they have directed their attention to adenosine A1 receptors present in the kidney and have found that the above object can be attained by utilizing the antagonism against the A1 receptor. Further, they have made intensive studies on a compoune exhibiting such antagonism and have found that the above object can be attained by the propenoic acid derivative which will be described below. The present invention has been accomplished on the basis of this finding.

Namely, the present invention relates to a propenoic acid derivative represented by the following general formula (I) or a pharmacologically acceptable salt thereof, and a remedy for renal failure which comprises the derivative as the active ingredient.

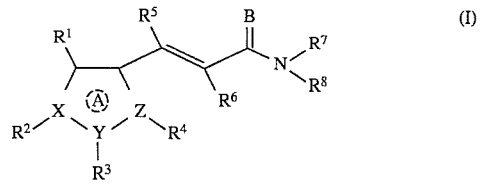

wherein A represents an aromatic ring;

X, Y and Z each represent carbon, nitrogen oxygen or sulfur;

$R^1$ represents optically substituted aryl or optionally substituted heteroaryl;

$R^2$, $R^3$ and $R^4$ may be the same or different from each other and each represents hydrogen, lower alkyl, lower alkenyl, lower alkynyl or a group represented by formula —W-Q (wherein W represents a group derived from lower alkyl; and Q represents optionally substituted aryl, optionally substituted heteroaryl, cycloalkyl, cyano, hydroxyl, lower alkoxy, acyloxy, carboxyl or a group represented by formula —$NR^9R^{10}$ (wherein $R^9$ and $R^{10}$ may be the same or different from each other and each represents hydrogen, lower alkyl, acyl, carbamoyl or alkylcarbamoyl, or alternatively $R^9$ and $R^{10}$ may represent, together with the nitrogen atom to which they are bonded, a cyclic group);

$R^5$ and $R^6$ may be the same or different from each other and each represents hydrogen or lower alkyl;

B represents oxygen or sulfur; and $R^7$ and $R^8$ may be the same or different from each other and each represents hydrogen, lower alkyl, lower alkoxy, optionally substituted aryl, optionally substituted arylalkyl, optionally substituted heteroaryl, optionally substituted heteroarylalkyl, optionally protected carboxyalkyl, a group represented by the following general formula:

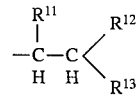

(wherein $R^{11}$ represents hydrogen, lower alkyl, optionally substituted aryl, optionally substituted arylalkyl or optionally substituted heteroaryl; $R^{12}$ represents hydrogen, hydroxyl, lower alkyl, lower alkoxy, optionally protected carboxyl, optionally substituted amino, optionally substituted aryl, optionally substituted heteroaryl, optionally substituted arylalkyl or optionally substituted heteroarylalkyl; and $R^{13}$ represents hydrogen, hydroxyl, lower alkyl, lower alkoxy, optionally substituted aryl or optionally substituted heteroaryl), or a group represented by formula —V-E [wherein V represents a group represented by formula —CO—, a group represented by formula —(CH$_2$)— or a group represented by the following formula:

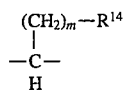

(wherein $R^{14}$ represents optionally substituted aryl or optionally substituted heteroaryl; and m is an integer of 0 or 1); and E represents optionally substituted aryl or optionally substituted heteroaryl], or alternatively, $R^7$ and $R^8$ may represent, together with the nitrogen atom to which they are bonded, a cyclic group which may be substituted; with the proviso that (1) when one to three of X, Y and Z are nitrogen atoms and one or all of the nitrogen atoms are each bonded to one of the adjacent atoms thereof through a double bond or (2) when one of X, Y and Z is nitrogen and another of them is oxygen or sulfur, then the corresponding X, Y and/or Z do not have their respective substituents $R^2$, $R^3$ and/or $R^4$ and that at least one of X, Y and Z, is unsubstituted.

The invention provides a method for preventing or treating a disease against which adenosine antagonism is efficacious, by administering a pharmacologically effective amount of the compound as defined above or a pharmacologically acceptable salt thereof to a subject who suffers or will suffer from the disease, and use of the compound or a pharmacologically acceptable salt thereof for manufacturing a preventing or treating agent for a disease against which adenosine antagonism is efficacious.

In the general formula (I), the lower alkyl defined with respect to $R^2$, $R^3$, $R^4$, $R^5$, $R^6$, $R^7$, $R^8$, $R^9$, $R^{10}$, $R^{11}$, $R^{12}$, $R^{13}$ and W refers to linear or brached alkyl having 1 to 6 carbon atoms and examples thereof include methyl, ethyl, propyl, isopropyl, butyl, isobutyl, sec-butyl, tert-butyl, pentyl (amyl), isopentyl, neopentyl, tert-pentyl, 2-methylbutyl, 3-methylbutyl, hexyl, isohexyl, 2-methylpentyl, 3-methylpentyl, 1,1-dimethylbutyl, 2,2-dimethylbutyl, 2,3-dimethylbutyl, 3,3-dimethylbutyl, 2-ethylbutyl, 1,1,2-trimethylpropyl, 1-ethyl-1-methylpropyl and 2-ethyl-3-methylpropyl, among which methyl and ethyl are preferable.

The above lower alkyl may be one substituted with halogen, for example, trifluoromethyl.

The lower alkenyl defined with respect to $R^2$, $R^3$ and $R^4$ refers to one derived from the above lower alkyl.

The lower alkynyl defined with respect to $R^2$, $R^3$ and $R^4$ refers to one derived from the above lower alkyl.

The lower alkoxy defined with respect to $R^7$, $R^8$, $R^{12}$, $R^{13}$ and Q refers to one derived from the above lower alkyl.

The aryl constituting the optionally substituted aryl as defined with respect to $R^1$, $R^7$, $R^8$, $R^{11}$, $R^{12}$, $R^{13}$, $R^{14}$, E and Q refers to phenyl, naphthyl or the like.

The heteroaryl constituting the optionally substituted heteroaryl as defined with respect to $R^1$, $R^2$, $R^3$, $R^4$, $R^7$, $R^8$, $R^{11}$, $R^{12}$, $R^{13}$, $R^{14}$, E and Q includes monocyclic groups such as pyridyl, furanyl, thienyl, imidazolyl, triazolyl, oxazolyl, pyrazyl, pyrimidyl, pyridazinyl, thiazyl and isoxazolyl; and fused heterocyclic groups such as benzimidazolyl, quinolyl, isoquinolyl and benzothiazolyl, among which pyridyl, thienyl, furanyl, quinolyl and benzimidazolyl are preferable.

The aryl constituting the optionally substituted arylalkyl as defined with respect to $R^7$, $R^8$, $R^{11}$ and $R^{12}$ is as defined above with respect to the optionally substituted aryl. The alkyl constituting it is as defined above with respect to the lower alkyl.

The heteroaryl constituting the optionally substituted heteroarylalkyl defined with respect to $R^7$, $R^8$ and $R^{12}$ is as defined above with respect to the optionally substituted heteroaryl. The alkyl constituting it is as defined above with respect to the above lower alkyl.

The acyl defined with respect to $R^9$ and $R^{10}$ refers to one derived from any carboxylic acid, and examples thereof include those derived from aliphatic saturated carboxylic acids, such as formyl, acetyl and propionyl; those derived from aliphatic unsaturated carboxylic acids, such as acryloyl, propioloyl and maleoyl; those derived from carbocyclic carboxylic acids, such as benzoyl, cinnamoyl and toluoyl; and those derived from heterocyclic carboxylic acids, such as furoyl, nicotinoyl and isonicotinoyl, among which formyl and acetyl are preferable.

The alkylcarbamoyl defined with respect to $R^9$ and $R^{10}$ refers to a carbamoyl group to which the above lower alkyl is bonded.

The acyloxy defined with respect to Q refers to one derived from the above acyl.

The cycloalkyl defined with respect to Q refers to one having 3 to 8 carbon atoms, preferably 5 or 6 carbon atoms.

The optionally protected carboxyl defined with respect to $R^{12}$ includes a free carboxyl group and carboxyl groups protected with lower alkyl groups such as methyl ant ethyl; haloalkyl groups such as 2,2,2-trichloroethyl, 2-iodoethyl and trichloromethyl; lower alkanoyloxyalkyl groups such as pivaloyloxymethyl, 1-acetoxyethyl and 2-acetoxyethyl; and heterocyclic groups such as 3-phthalidyl. Further, it also includes various acid amides. In short, the protected carboxyl group may be any one which can be cleaved by any means in vivo to form a carboxyl group.

The optionally protected carboxyl constituting the optionally protected carboxyalkyl defined with respect to $R^7$ and $R^8$ is as defined with respect to the above optionally protected carboxyl.

The pharmacologically acceptable salt according to the present invention includes inorganic acid salts such as hydrochloride, sulfate, hydrobromide, nitrate and phosphate; and organic acid salts such as formate, acetate, trifluoroacetate, maleate, fumarate, tartrate, methanesulfonate, benzenesulfonate and toluenesulfonate.

Some of these salts form hydrates and it is needless to say that the present invention includes such hydrates.

As will be understood from the chemical structure, the compound of The present invention may be present as various isomers including geometrical isomers such as cis and trans isomers and optical isomers such as d- and l-isomers. It is needless to say that the present invention includes all of The isomers.

Representative processes for preparing the compound of the present invention will now be described.

Preparation Process 1

Among the compounds represented by the general formula (I), a compound represented by the following general formula:

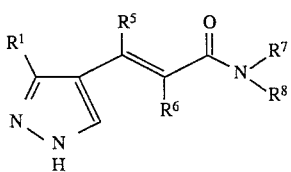

(wherein $R^1$, $R^5$, $R^6$, $R^7$ and $R^8$ are each as defined above) can be prepared by the following process:

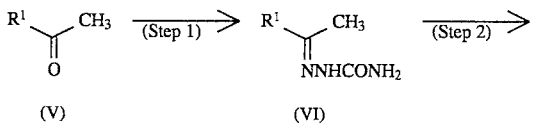

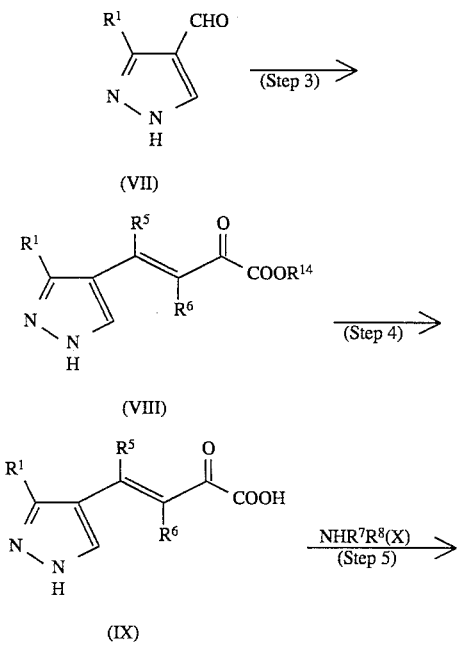

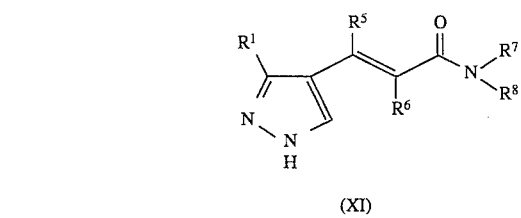

wherein $R^1$, $R^5$, $R^6$, $R^7$ and $R^8$ are each as defined above; and $R^{14}$ represents a carboxyl-protective group.

(Step 1)

In this step, a compound represented by the general formula (VI) is prepared by reacting a ketone compound represented by the general formula (V) with semicarbazide hydrochloride in the conventional manner.

The solvent to be used in this reaction is preferably an aqueous one containing a suitable amount of an alcohol, and the reaction temperature preferably ranges from room temperature to the refluxing temperature of the solvent.

(Step 2)

In this step, the compound (VI) prepared in the Step 1 is subjected to ring-closure reaction in the conventional manner.

Precisely, at least two equivalents of phosphorus oxychloride is dropped into dimethylformamide and reacted with the compound (VI). The reaction temperature preferably ranges from room temperature to refluxing temperature.

(Step 3)

In this step, the compound (VII) prepared in the Step 2 is converted into an imidazole derivative represented by the general formula (VIII) through the Wittig reaction.

Precisely, the imidazole derivative (VIII) can be prepared by treating a Wittig reagent or a Wittig-Horner-Emmons reagent with a base in an organic solvent and reacting the aldehyde (VII) with the resulting agent. The organic solvent may be any one inert to the reaction and examples thereof include ethers such as tetrahydrofuran and dioxane; and hydrocarbons such as benzene. The base is preferably an alkali metal hydride such as sodium hydride, an alkoxide such as potassium t-butoxide, or an amide such as sodium amide or lithium diisopropylamide.

The reaction temperature ranges from 0° C. to the refluxing temperature of the solvent.

(Step 4)

In this step, the propenoic acid derivative (VIII) prepared in the Step 3 is freed from the carboxyl-protective group in the conventional manner.

This deblocking can be conducted by hydrolyzing the derivative (VIII) under basic or acidic conditions.

When the deblocking is conducted under basic conditions, it is preferably to use sodium hydroxide or potassium hydroxide, while when it is conducted under acidic conditions, it is preferable to use hydrochloric or sulfuric acid. The solvent to be used in the deblocking is preferably a water-containing organic solvent, and the organic solvent may be any one inert to the reaction.

The reaction temperature ranges from 0° C. to the refluxing temperature of the solvent.

(Step 5)

In this step, the propenoic acid derivative (IX) prepared in the Step 4 is condensed with an amine (X).

The solvent to be used in this reaction may be any one inert to the reaction and examples thereof include tetrahydrofuran, dioxane, ethyl acetate, benzene, dimethylformamide, dichloromethane, chloroform and acetonitrile.

The condensation can be conducted by any conventional method. Examples of the method include the 1,3-dicyclohexylcarbodiimide (hereinafter abbreviated to "DCC") method, the DCC-[1-hydroxybenzotriazole (hereinafter abbreviated to "HOBT") method, the DCC-[N-hydroxysuccinimide (hereinafter abbreviated to "HONS")] method, and improved methods based on these methods, such as the [1-(3-dimethylaminopropyl)-3-ethylcarbodiimide (hereinafter abbreviated to "EDCl")]-HOBt method.

Alternatively, the compound (IX) may be converted into a conventional reactive derivative thereof prior to the condensation with the amine.

Examples of the conventional reactive derivative include acid halides prepared by treating the compound (IX) with phosphorus oxychloride or thionyl chloride; mixed acid anhydrides prepared by reacting the compound (IX) with isobutyl chloroformate (IBCF), 1-ethoxycarbonyl-2-ethoxy-1,2-dihydroquinoline (EEDQ) or ethyl chlorocarbonate; and acid azides prepared from the compound (IX) by the use of diphenylphosphoryl azide (DPPA). Further, the compound (IX) may be converted into an active ester such as p-nitrophenylphenyl (—ONp) ester or N-hydroxysuccinimide (—ONSu) ester. The objective compound (XI) can be prepared by reacting such a reactive derivative with the amine (X) in an organic solvent.

The reaction temperature ranges from 0° C. to the refluxing temperature of the solvent.

Preparation Process 2

Among the compounds represented by the general formula (I), a compound represented by the general formula (XII) or (XIII) can be prepared by the following process:

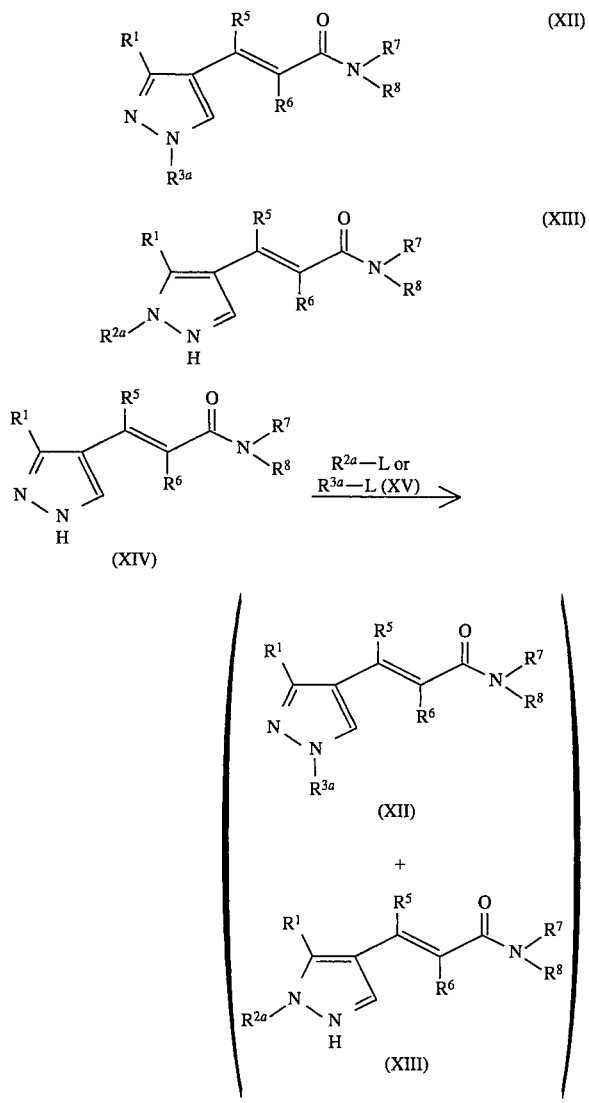

wherein $R^1$, $R^5$, $R^6$, $R^7$ and $R^8$ are each as defined above; $R^{2a}$ and $R^{3a}$ each represent a group represented by formula —W-Q (wherein W and Q are each as defined above); and L represents a leaving group such as a halogen or p-toluenesulfonyl.

Precisely, the objective imidazole derivative represented by the general formula (XII) or (XIII) is prepared by reacting an imidazole compound represented by the general formula (XIV) with a compound represented by the general formula (XV) in the presence of a base.

Although the compounds (XII) and (XIII) are generally obtained as a mixture of both, each compound can be isolated by subjecting the mixture to column chromatography.

In the compound (XV), L represents a leaving group such as a halogen or p-toluenesulfonyl.

The solvent to be used in the reaction may be any organic one inert to the reaction and preferable examples thereof include dimethylformamide, toluene, dioxane and tetrahydrofuran. The base is preferably an alkali metal hydride such as sodium hydride, an alkali metal alkoxide such as potassium t-butoxide or sodium methoxide, or lithium diisopropylamide.

The reaction temperature ranges from about —50° C. to the refluxing temperature of the solvent.

Preparation Process 3

Among the compounds represented by the general formula (I), a compound represented by the general formula (XVI):

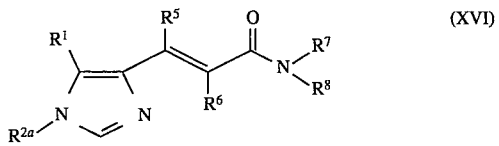

(wherein $R^1$, $R^{2a}$, $R^5$, $R^6$, $R^7$ and $R^8$ are each as defined above) or the general formula (XVII):

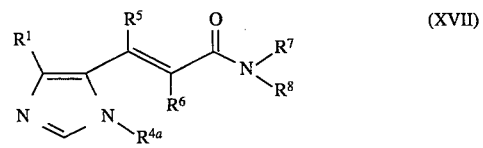

(wherein $R^1$, $R^5$, $R^6$, $R^7$ and $R^8$ are each as defined above; and $R^{4a}$ represents a group represented by formula —W-Q, wherein W and Q are each as defined above) can be prepared by the following process:

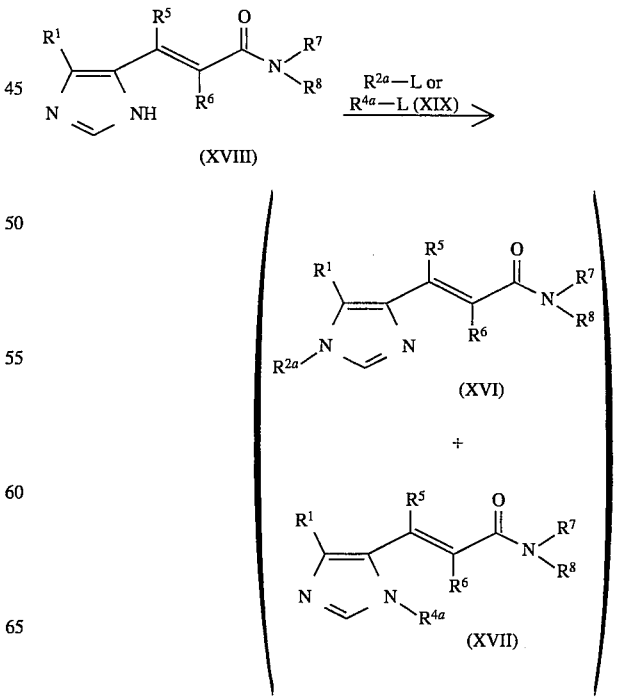

wherein $R^1$, $R^{2a}$, $R^{4a}$, $R^5$, $R^6$, $R^7$ and $R^8$ are each as defined above.

Precisely, the objective compound (XVI) or (XVII) is prepared by reacting a compound represented by the general formula (XVIII) with a compound (XIX) in the presence of a base.

The solvent to be used in the reaction may be any organic one inert to the reaction and examples thereof include ethers such as tetrahydrofuran and dioxane; hydrocarbons such as toluene; dimethylformamide and acetone.

Preferable examples of the base include alkali metal hydrides such as sodium hydride; alkali metal alkoxides such as potassium t-butoxide and sodium methoxide; and lithium diisopropylamide.

The reaction temperature preferably ranges from about −50° C. to the refluxing temperature of the solvent.

Preparation Process 4

A compound represented by the general formula (I) wherein B is sulfur can be prepared by the following process:

The reagent to be used in the conversion may be any conventional one and examples thereof include Lawson reagent and phosphorus pentasulfide.

The solvent to be used in the reaction may be any organic one inert to the reaction and preferable examples thereof include hydrocarbons such as toluene and benzene; ethers such as dioxane and tetrahydrofuran; and chloroform.

The reaction temperature preferably ranges from room temperature to the refluxing temperature of the solvent.

Preparation Process 5

Among the compounds represented by the general formula (I), a compound represented by the general formula (XVIII):

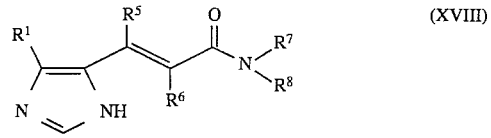

(wherein $R^1$, $R^5$, $R^6$, $R^7$ and $R^8$ are each as defined above) can also be prepared by the following process:

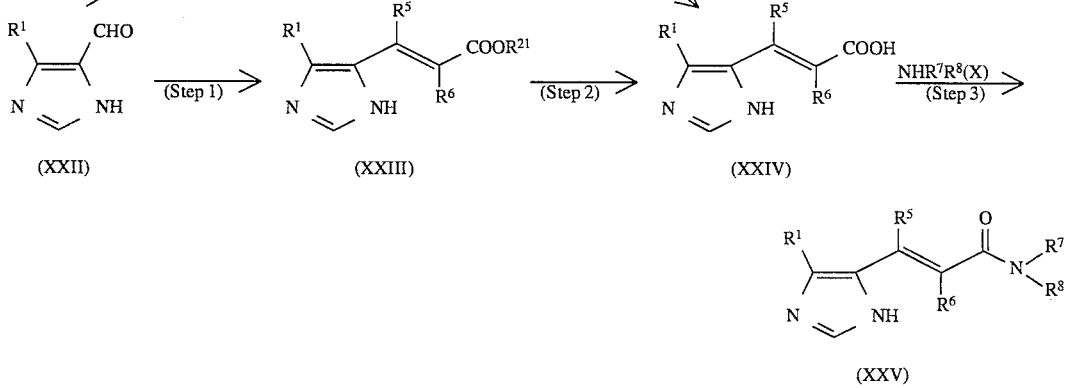

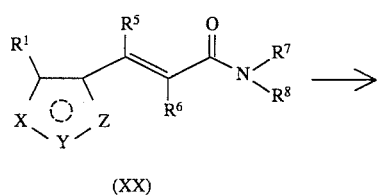

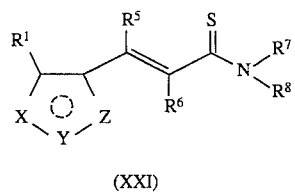

wherein $R^1$, $R^5$, $R^6$, $R^7$, $R^8$, X, Y and Z are each as defined above.

Precisely, the objective compound (XXI) is prepared by converting a ketone compound represented by the general formula (XX) into the corresponding thioketone compound in the conventional manner.

wherein $R^1$, $R^5$, $R^6$, $R^7$ and $R^8$ are each as defined above; and $R^{21}$ represents a carboxyl-protective group.

(Step 1)

In this step, a propenoic acid derivative represented by the general formula (XXIII) is prepared from an imidazolylaldehyde represented by the general formula (XXII) through the Wittig reaction. The propenoic acid derivative (XXIII) is prepared by treating a Wittig reagent or a Wittig-Horner-Emmons reagent with a base in a solvent and reacting the aldehyde with the resulting reagent.

The solvent may be any organic one inert to the reaction and examples thereof include ethers such as tetrahydrofuran and dioxane; and hydrocarbons such as benzene.

The base may be any conventional one and preferable examples thereof include alkali metal hydrides such as sodium hydride; alkali metal alkoxides such as potassium t-butoxide; and amides such as sodium amide and lithium diisopropylamide.

(Step 2)

In this step, the propenoic acid derivative (XXIII) prepared in the Step 1 is hydrolyzed in the conventional manner to remove the carboxyl-protective group.

This hydrolysis is conducted under the acidic condition with hydrochloric or sulfuric acid or under the alkaline condition with sodium hydroxide or potassium hydroxide.

The solvent to be used in the reaction may be any conventional one inert to the reaction.

The reaction temperature ranges from 0° C. to the refluxing temperature of the solvent.

Alternatively, the propenoic acid derivative represented by the general formula (XXIV) can also be prepared directly from the imidazolylaldehyde (XXII) without the step 2. For example, the compound (XXIV) can be prepared by subjecting the compound (XXII) to the Knoevenagel condensation. This condensation is conducted in the presence of a catalytic amount of an amine and preferable examples thereof include ammonium salts and primary and secondary amines.

The solvent to be used in the above condensation may be any organic one inert to the condensation and preferable examples thereof include hydrocarbons such as benzene and toluene.

The reaction temperature preferably ranges from room temperature to the refluxing temperature of the solvent.

(Step 3)

In this step, an objective compound (XXV) is prepared by condensing the propenoic acid derivative (XXIV) prepared in the above Step 2 with an amine represented by the general formula (X). The solvent to be used in this reaction may be any organic one inert to the reaction and examples thereof include ethers such as tetrahydrofuran and dioxane; hydrocarbons such as benzene; dichloromethane, chloroform, acetonitrile and dimethylformamide.

All of the conventional condensation methods can be employed in this step, and examples thereof include the DCC method; the DCC-additive methods such as the DCC-HOBT method and DCC-HONSu method; and improved methods based on these methods, such as the EDC1-HOBT method.

Alternatively, the objective compound (XXV) can also be prepared with a reactive derivative of the compound (XXIV).

Precisely, the compound (XXV) can also be prepared by converting the compound (XXIV) into an acid halide by treatment with thionyl chloride or phosphorus oxychloride, into an acid azide by the use of isobutyl chloroformate (IBCF), 1-ethoxycarbonyl-2-ethoxy-1,2-dihydroxyquinoline (EEDQ) or chloroazide (DPPA), or into an active ester such as p-nitrophenylphenyl (—ONp) ester or N-hydroxysuccinimide (—ONSu) ester, and reacting the reactive derivative thus prepared with the amine (X) in the above organic solvent.

Both the former reaction and the latter reaction may be conducted at a temperature ranging from 0° C. to the refluxing temperature of the solvent.

The processes for preparing representative starting compounds used in the above Preparation processes will now be described.

Preparation Process A

When the amine (X) used in the Preparation process 1 is one represented by the formula (XXVI):

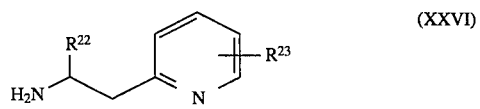

(XXVI)

(wherein $R^{22}$ and $R^{23}$ each represent a group represented by formula —V-E, wherein V and E are each as defined above), this amine can be prepared by the following process:

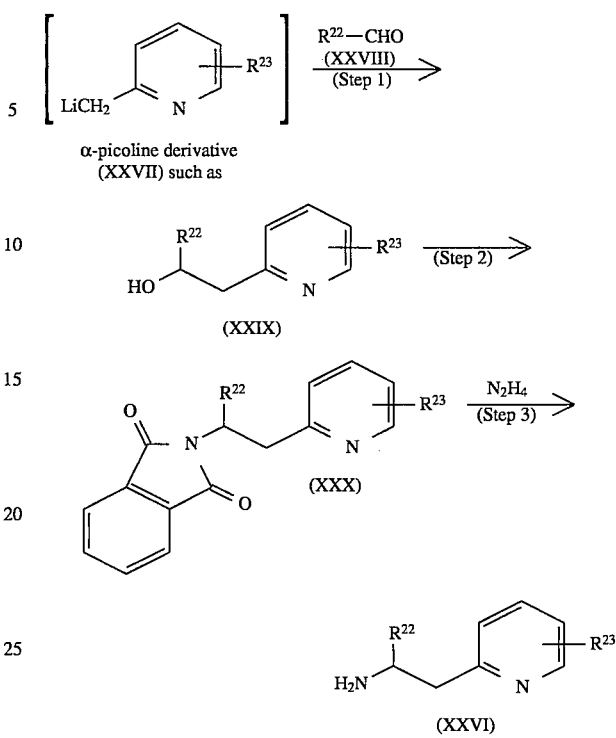

wherein $R^{22}$ and $R^{23}$ are each as defined above.

(Step 1)

In this step, an alcohol represented by the general formula (XXIX) is prepared by reacting an α-picoline derivative (XXVII) with an aldehyde represented by the general formula (XXVIII) in the presence of a base.

The base is preferably a strong one such as n-butyllithium.

It is preferable that the reaction be conducted at low temperature, still preferably at −78° to −20° C.

(Step 2)

In this step, a phthalimide derivative represented by the general formula (XXX) is prepared by subjecting the alcohol (XXIX) prepared in the Step 1 to the Mitsunobu reaction.

The organic solvent used in this reaction may be any organic one inert to the reaction and preferable examples thereof include tetrahydrofuran, dioxane, chloroform and benzene. This step is conducted by dissolving the alcohol (XXIX) in such an organic solvent and adding triphenylphosphine, phthalimide and diethyl azodicarboxylate to the obtained solution. The order of addition of these compounds to the solvent may be suitably changed.

The reaction temperature may range from −50° to 60° C., preferably from −30° C. to room temperature.

(Step 3)

In this step, the objective amine (XXVI) is prepared by reacting the phthalimide derivative (XXX) prepared in the Step 2 with hydrazine in an alcohol.

The reaction temperature may range from room temperature to the refluxing temperature of the solvent.

Preparation Process B

Among the amines (X) used in the Preparation process 1, a compound (XXXIII) represented by formula $H_2N-NR^{24}-CH_2-R^{25}$ can also be prepared by the following process:

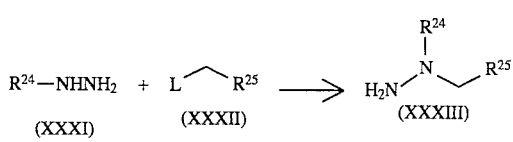

wherein $R^{24}$ and $R^{25}$ may be the same or different from each other and each represents optionally substituted aryl or optionally substituted heteroaryl; and L represents a leaving group such as a halogen or p-toluenesulfonyl.

Precisely, the objective compound (XXXIII) is prepared by reacting a compound represented by the general formula (XXXI) with a compound represented by the general formula (XXXII) in an organic solvent.

The organic solvent may be any one inert to the reaction and preferable examples thereof include alcohols such as methanol, ethanol and isopropanol; ethers such as dioxane and tetrahydrofuran; hydrocarbons such as toluene, and dimethylformamide.

The reaction temperature can be arbitrarily selected within the range of from room temperature to the refluxing temperature of the solvent.

Preparation Process C

Among the amines (X) used in the Preparation process 1, a compound (XXXVII) represented by the general formula: $H_2N\text{-}CHR^{26}\text{-}CH_2\text{-}R^{27}$ (wherein $R^{26}$ and $R^{27}$ may be the same or different from each other and each represents optionally substituted aryl or optionally substituted heteroaryl) can be prepared by the following process:

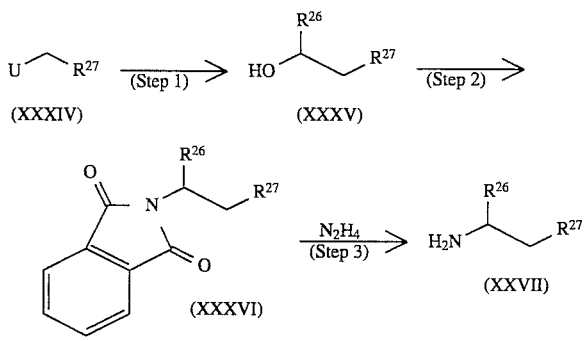

wherein $R^{26}$ and $R^{27}$ are each as defined above; and U represents halogen.

Precisely, an alcohol (XXXV) is prepared by reacting a halide represented by the general formula (XXXIV) with a suitable metal to form an active derivative and reacting this active derivative with an aldehyde.

In particular, any conventional process may be used in the above reaction and examples thereof include the Barbier reaction and the Grignard reaction.

According to the Barbier reaction, the alcohol (XXXV) is prepared by reacting the compound (XXXIV) with lithium in a solvent inert to the reaction and thereafter reacting the obtained product with an aldehyde. Preferable examples of the solvent include ethers such as tetrahydrofuran and dioxane; and hydrocarbons such as toluene. Further, desirable results can be attained by conducting ultrasonic irradiation in the stage of preparing the active derivative.

According to the Grignard reaction, the alcohol (XXXV) is prepared by reacting the compound (XXXIV) with magnesium in an organic solvent to form an active derivative and reacting this active derivative with an aldehyde.

The reaction temperature may be arbitrarily selected between −50° C. and the boiling point of the solvent.

Preparation Process D

Among the compounds prepared in the Preparation process A, a chiral compound (XXXX) can be prepared by the following process:

(1)

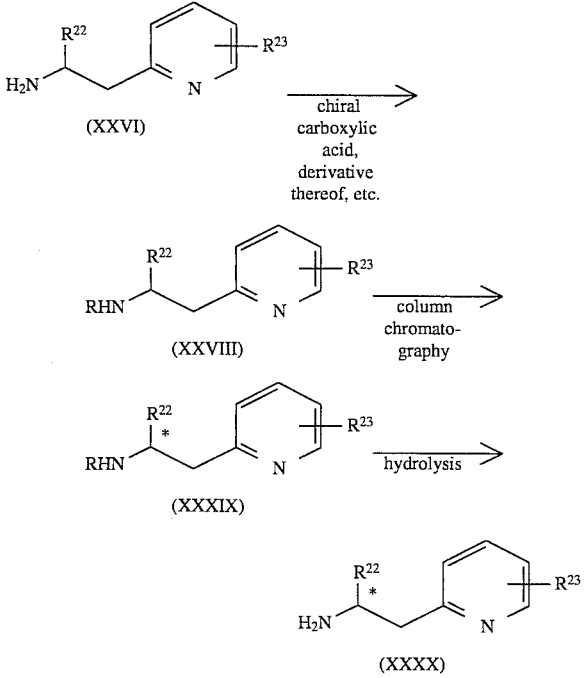

The objective optically active amine (XXXX) is prepared by condensing the racemic compound (XXVI) prepared in the Preparation process A with a chiral carboxylic or sulfonic acid or a derivative thereof to form a diastereomer mixture (XXXVIII), separating the diastereomer mixture (XXXVIII) into chiral compounds (XXXIX) by the conventional column chromatography and hydrolyzing each of the compounds (XXXIX) under acidic conditions.

The condensation of the compound (XXVI) into the compound (XXXVIII) may be conducted by the conventional method. Examples of the method include the DCC method, the DCC-HOBT method, the DCC-HONSu method, and improved methods based on these methods, such as the EDC1-HOBt method. The solvent to be used in this condensation may be any organic one inert to the reaction and examples thereof include tetrahydrofuran, dioxane, ethyl acetate, benzene, dimethylformamide, dichloromethane, chloroform and acetonitrile.

The above reactive derivative includes acid halides, acid anhydrides, acid azides and active esters.

The chiral carboxylic acid and derivative thereof include (+)-mandelic acid, (−)-mandelic acid, chiral amino acid derivatives, (+)-tartaric acid, (+)-camphorsulfonic acid, (+)-phenylethanesulfonic acid, (−)-phenylethanesulfonic acid, and derivatives thereof.

The hydrolysis of the compound (XXXIX) into the compound (XXXX) is conducted in an aqueous medium under strongly acidic condition with hydrochloric or sulfuric acid, generally at a temperature ranging from room temperature to refluxing one.

(2)

Alternatively, the optically active compound (XXXX) can also be prepared directly from the racemic compound (XXVI) by frictional crystallization.

Precisely, the chiral amine can be prepared by reacting the compound (XXVI) with a chiral carboxylic or sulfonic acid to form a salt mixture, subjecting the mixture to fractional recrystallization repeatedly to conduct purification, and converting the obtained pure salt into an amine.

The chiral carboxylic or sulfonic acid used as the resolving agent may be selected from among those described in the above paragraph (1).

Examples of the solvent usable in the fractional recrystallization include acetone, methanol, ethanol, isopropanol, water, and mixtures of two or more of them.

The reaction temperature may be arbitrarily selected between −20° C. and the refluxing temperature of the solvent.

Pharmacological Experimental Examples will now be described to illustrate the usefulness of the compounds according to the present invention in more detail.

PHARMACOLOGICAL EXPERIMENTAL EXAMPLE

In this example, (+)-(E)-N-{1-(4-chloropyridin-2-yl)-2-(pyridin-2-yl)ethyl}-3-{3-(3-fluorophenyl)-1H-pyrazol-4-yl}-2-propenamide which is a representative example of the compound of the present invention was used as the rest compound.

1. Activity against glycerol-induced renal trouble model (i) Experimental method Fisher 344 male rats aged 8 weeks and weighing 200 to 230 g were kept without water for 18 hours prior to the use. Thereafter, the test compound was orally administered forcedly to the test group of rats in an amount of 0.3 mg/5 ml/kg, while a solvent [2% Tween 80 solution] to the control group of rats in an amount of 5 ml/kg. After 60 minutes from the administration of the test compound or solvent, a 50% solution of glycerol in physiological saline was intramuscularly administered to each rat through both left and right femoral muscles in an amount of 10 ml of kg. After the completion of the intramuscular administration, the rats were watered. After about 24 hours, the rats were etherized and blood was sampled from each rat. The blood samples thus prepared were each centrifuged to collect serum, which was analyzed for urea nitrogen and creatinine.

(ii) Experimental results

The results are given in Table 1.

TABLE 1

|  | Serum urea nitrogen (mg/dl) | serum creatinine (mg/dl) |
|---|---|---|
| Control group | 185.4 ± 3.2 | 4.76 ± 0.21 |
| Test group | 142.4 ± 10.5* | 3.47 ± 0.30* |

*P < 0.05 (unpaired t-test vs control)

2. Activity against cisplatin-induced gastric trouble model (i) Experimental method Cisplatin was subcutaneously administered to Fisher 344 male rats aged 7 weeks and weighing 170 to 200 g in an amount of 6 mg/5 ml/kg. Immediately after the administration, the test compound was orally administered forcedly to the test group of rats in an amount of 1 mg/5 ml/kg, while a solvent (2% Tween 80 solution) to the control group of rats in an amount of 5 ml/kg. Six hours after the administration, the administration of the test compound and the solvent to the test group and the control group respectively was conducted in a similar manner to that described above. Thereafter, the same administration was repeated on the next day twice, and on the third and forth days each once. On the fifth day, the rats were etherized and blood was sampled from each rat. The blood samples thus prepared were analyzed for serum urea nitrogen and creatinine.

(ii) Experimental results

The results are given in Table 2.

TABLE 2

|  | Serum urea nitrogen (mg/dl) | serum creatinine (mg/dl) |
|---|---|---|
| Control group | 93.4 ± 6.5 | 2.15 ± 0.16 |
| Test group | 52.9 ± 2.3* | 1.49 ± 0.04* |

*P < 0.05 (unpaired t-test vs control)

3. Diuretic activity (1) Experimental method

Fisher male rats aged 8 weeks and weighing 190 to 210 g were fasted for 18 hours prior to the use. The test compound was orally administered forcedly to the test group of rats in a state dispersed in a 0.4% solution of Tween 80 in physiological saline in an amount of 1 mg/25 ml/kg, while a 0.4% solution of Tween 80 in physiological saline to the control group of rats in the same amount as that administered to the test group. Immediately after the administration, the rats were put in individual metabolism cages respectively to collect urine from each rat for 2 hours. The urinary volume of each rat was determined and thereafter the urine was examined for uric acid concentration to calculate the amount of uric acid egested. The control group was composed of six rats, while the test group three rats. The amounts of uric acid excreted from the rats of each group were averaged out to determine the increment of the excretion of uric acid based on the averages.

(ii) Experimental results

The urinary volume of the test group was 605% and the amount of uric acid excreted therefrom was 166% when the urinary volume and the amount of the excreted uric acid of the control group are taken each as 100%.

4. Adenosine antagonism (i) Experimental method

Hartley male guinea pigs weighing 250 to 400 g were beaten to death. The heart was immediately extirpated from each guinea pig and put in the Krebs-Heuseleit solution saturated with a gas mixture comprising 95% of oxygen and 5% of carbon dioxide. Thereafter, the right atrium was extirpated from the heart. The samples thus preparer were each vertically suspended in a Magnus tube (capacity: 6 ml) filled with a nutrient liquid at 37° C. and the same gas mixture as that used above was passed through the tube.

The change in tension was isometrically determined under a load of about 0.5 g and the spontaneous heart rate was measured and recorded with a cardiotachometer by utilizing the signal of the change as a trigger.

After the stabilization of the sample, $10^{-5}$ mol of dipyridamole was added to each Magnus tube. Thereafter, the test compound was added directly to each of the Magnus tubes of the test group in a state dissolved in DMSO, while a solvent (DMSO) to each of the Magnus tubes of the control group in the same amount as that added to each Magnus tube of the test group. The resulting Magnus tubes was allowed to stand for 20 minutes. Thereafter, $10^{-8}$ to $10^{-2}$ mol of adenosine was cumulatively added to each Magnus tube until the spontaneous heart beat discontinued.

The $EC_{50}$ value with respect to the heart rate lowering effect of adenosine was calculated and the adenosine antagonism was represented by $pA_2$ value (–log M).

(ii) Experimental result $pA_2$ value=10.41

As described above, the compound of the present invention exhibits adenosine antagonism and is effective in the prevention and treatment of diseases against which this antagonism is efficacious.

Specific examples of such diseases include edemas such as hepatic, renal and heart edemas; hypertension; and acute and chronic renal failures. In particular, renal failure, as described in the above pharmacological Experimental Example, can be inhibited from sideration by administering the compound of the present invention in advance. In other words, it is apparent that the compound of the present invention is also effective in preventing the above diseases.

Further, the compound of the present invention is less toxic and highly safe, thus being valuable also in this sense.

The compound of the present invention is orally or parenterally administered as a protective and therapeutic agent for the above diseases. The dose thereof varies depending upon the symptom of a patient and the extent thereof; the age, sex, weight and drug sensitivity of a patient; the method, timing and interval of administration; the kind and properties of the pharmaceutical preparation; the kind of the drug to be administered therewith and so on, and is not particularly limited. For example, when the compound is orally administered, the dose per adult a day is generally about 0.1 to 1000 mg, preferably 0.5 to 500 mg, still preferably 1 to 10 mg, which may be administered in one to several portions, preferably one or two portions a day. When it is administered as an injection, the dose is 0.1 to 100 μg/kg.

The pharmaceutical preparations according to the present invention are prepared by the use of the conventional carrier in the conventional manner. More precisely, a solid preparation for oral administration according to the present invention is prepared by adding a filler and, if necessary, a binder, disintegrator, lubricant, color and/or corrigent to an active ingredient and shaping the obtained mixture into a tablet, coated tablet, granule, powder or capsule.

Examples of the filler include lactose, corn starch, sucrose, glucose, sorbitol, crystalline cellulose and silicon dioxide; those of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; those of the lubricant include magnesium stearate, talc, polyethylene glycol, silica and hardened vegetable oil; those of the color include those authorized as pharmaceutical additives; and those of the corrigent include cocoa powder, menthol, aromatic powder, mentha oil, borneol and powdered cinnamon bark. Of course, the tablet and granule may be suitably coated with sugar, gelatin or the like, if necessary. An injection according to the present invention is prepared by adding a pH regulator, buffer, stabilizer and/or solubilizing agent to an active ingredient at need and formulating the mixture into an injection for subcutaneous, intramuscular or intravenous administration by the conventional method.

EXAMPLE

Examples will now be described to facilitate the understanding of the present invention, though it is needless to say that the present invention is not limited to them. Further, Preparative Examples will be described prior to the Examples to describe the preparation of the starting compounds used for preparing the compounds of the present invention.

PREPARATIVE EXAMPLE 1

3-Fluormacetophenone semicarbazone

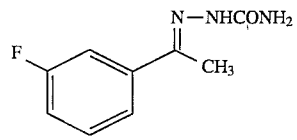

500 ml of an aqueous solution of 66.9 g of sodium acetate and 49.9 g of semicarbazide hydrochloride were added to 50 ml of an ethanolic solution of 51.2 g of 3-fluoroacetophenone. The obtained mixture was heated under reflux for 3 hours to precipitate crystals, which were recovered by filtration. Yield: 72.3 g.

m.p.: 205°~207° C.

$^1$H-NMR (DMSO-$d_6$) δ (ppm) 2.16(3H, s) 6.58(2H, br-s). 7.12(1H, dr, J=8 Hz, 1 Hz) 7.37(1H, dd, J=8 Hz, 8 Hz) 7.61(1H, d, J=8 Hz) 7.50(1H, dr, J=8 Hz, 1 Hz) 9.39(1H, s)

PREPARATION EXAMPLES 2 AND 3

The following compounds were prepared in a similar manner to that of the Preparative Example 1.

PREPARATIVE EXAMPLE 2

2-Acetyl-5-methylthiophene semicarbazone

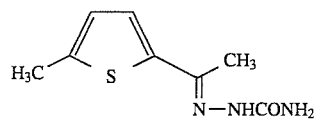

m.p.: 215°~218° C.

$^1$H-NMR (DMSO-$d_6$) δ (ppm) 2.15(3H, s) 6.24(2H, br-s) 6.73(1H, d, J =3 Hz) 7.15(1H, d, J=3 Hz) 9.35(1H, s)

PREPARATIVE EXAMPLE 3

2-Acetyl -5-chlorothiophene semicarbazone

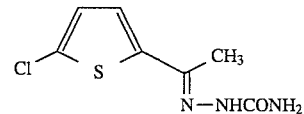

$^1$H-NMR (DMSO-$d_6$) δ (ppm) 2.16(3H, s) 6.32(2H, br-s) 7.04(1H, d ) J=4 Hz) 7.21 (1H, d, J=4 Hz) 9.49 (1H, s)

PREPARATIVE EXAMPLE 4

3-(3-Flurorphenyl)-1H-4-pyrazolecarbaldehyde

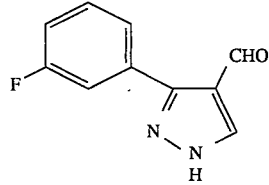

The synthesis of the title compound was conducted by the use of the 3-fluoroacetophenone prepared in the Preparative Example 1 according to the process described in J. Heterocyclic Chem., 7, 25 (1970), and the obtained crude product was recrystallized from ethanol/water. Yield: 48.5 g.

m.p.: 132°~134° C.

$^1$H-NMR (CDCl$_3$) δ (ppm) 7.25~7.32(1H, m) 7.42~7.52(m, 3 H) 8.18(1H, s) 10.00(1H, s)

PREPARATIVE EXAMPLES 5 AND 6

The following compounds were prepared in a similar manner to that the Preparative Example 4.

EXAMPLE 5

3-(5-Methylthiophen-2-yl)-1H-4-pyrazolecarbaldehyde

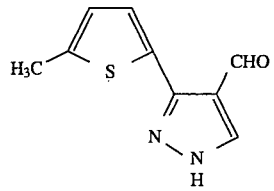

The title compound was prepared in a similar manner to that of the Preparative Example 4.

m.p.: 97°~99° C.

$^1$H-NMR (CDCl$_3$) δ (ppm) 2.54(3H, s) 6.81(1H, d, J=4 Hz) 7.54 (1H, d, J=4 Hz) 8.13(1H, s) 10.06(1H, s)

PREPARATIVE EXAMPLE 6

3-(5-Chlorothiophen-2-yl)-1H-4-pyrazolecarbaldehyde

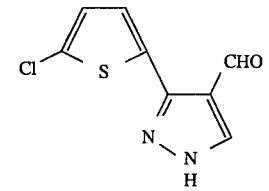

$^1$H-NMR (CDCl$_3$) δ (ppm) 6.95 (1H, d, J=4 Hz) 7.74 (1H, d, J=4 Hz) 8.17(1H, s) 10.03(1H, s)

PREPARATIVE EXAMPLE 7

Ethyl (E)-(3-phenyl-1H-pyrazol-4-yl)-2-propenoate

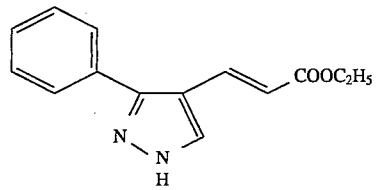

180 ml of a solution of 49.3 g of ethyl diethylphosphonoacetate in tetrahydrofuran was dropped into 30 ml of a suspension of 8.8 g of 60% sodium hydride in tetrahydrofuran under cooling with ice. The obtained mixture was stirred for 30 minutes, followed by the addition thereto of 250 ml of a solution of 34.4 g of 3-phenyl-1H-pyrazole-4-carbaldehyde in tetrahydrofuran under cooling with ice. The resulting mixture was stirred at room temperature for 12 hours, treated with an aqueous solution of ammonium chloride, and extracted with ethyl acetate. The organic phase was dried and concentrated. The residue was recrystallized from isopropyl ether/n-hexane. Yield: 36.3 g.

m.p.: 91°~94° C.

$^1$H-NMR (CDCl$_3$) δ (ppm) 1.31(3H, t, J=7 Hz) 4.23(2H, q, J=7 Hz) 6.26(1H, d, J=16 Hz) 7.43~7.55(5H, m) 7.67(1H, d, J=7 Hz) 7.85(1H, s)

PREPARATIVE EXAMPLES 8 TO 11

The following compounds were each prepared in a similar manner to that of the Preparative Example 7.

PREPARATIVE EXAMPLE 8

Ethyl (E)-{3-(3-fluorophenyl)-1H-pyrazol-4-yl}-2-propenoate

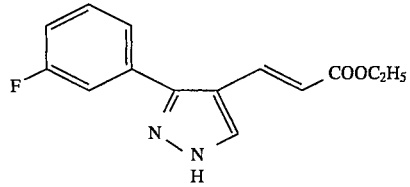

m.p.: 106°~108° C.

$^1$H-NMR (CDCl$_3$) δ (ppm) 1.32 (3H, t, J=7 Hz) 4.24 (2H, q, J=7 Hz) 6.27(1H, d, J=16 Hz) 7.15(1H, m) 7.11–7.32 (2H, m) 7.45(1H, m) 7.66(1H, d, J=16 Hz) 7.88(1H, s)

PREPARATIVE EXAMPLE 9

Ethyl (E)-{3-(5-methylthiophen-2-yl)-1H-pyrazol-4-yl}-2-propenoate

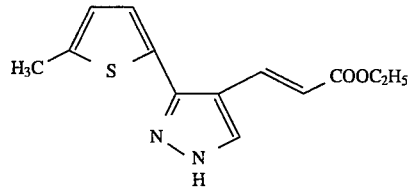

¹H-NMR (CDCl₃) δ (ppm) 1.32(3H, t, J=7 Hz) 2.53(3H, s) 4.25(2H, d, J=7 Hz) 6.26 (1H, d. J=16 Hz) 6.79 (1H, d, J=4 Hz) 7.08(1H, d, J=4 Hz) 7.80(1H, d, J=16 Hz) 7.85(1H, s)

PREPARATIVE EXAMPLE 10

Ethyl (4)-2-methyl-{3-(5-methylfuran-2-yl)-1H-pyrazol-4-yl}-2-propenoate

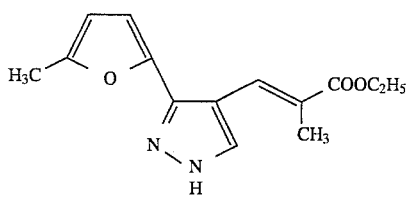

¹H-NMR (CDCl₃) δ (ppm) 1.36(3H, t, J=7 Hz) 2.14(3H, s) 2.39(3H, s) 4.27(2H, q, J=7 Hz) 6.13(1H, d, J=3 Hz) 6.59(1H, d, J=3 Hz) 7.27(1H, s) 7.83(1H, s)

PREPARATIVE EXAMPLE 11

Ethyl (E)-3-{3-(5-chlorothiophen-2-yl)-1H-pyrazol-4-yl}-2-propenoate

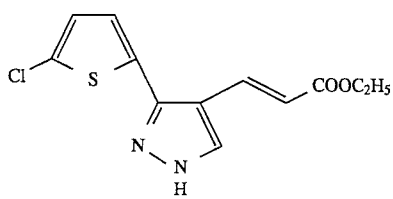

¹H-NMR (CDCl₃) δ (ppm) 1.33(3H, t, J=7 Hz) 4.26(2H, q, J=7 Hz) 6.28(1H, d, J=15 Hz) 6.96(1H, d, J=4 Hz) 7.07(1H, d, J=4 Hz) 7.73 (1H, d, J=15 Hz) 7.87(1H, s)

PREPARATIVE EXAMPLE 12

(E)-(3-Phenyl-1H-pyrazol-4-yl)-2-propenoic acid

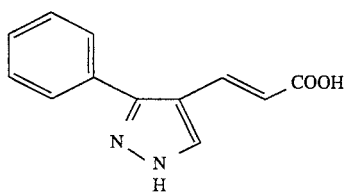

200 ml of ethanol and 180 ml of a 10% aqueous solution of sodium hydroxide were added to 35.7 g of the ethyl (E)-(3-phenyl-1H-pyrazol-4-yl)-2-propenoate prepared in the Preparative Example 7. The obtained mixture was heated under reflux for 1.5 hours and concentrated to about two-thirds of the initial volume. The concentrate was neutralized with 3N hydrochloric acid to precipitate crystals, which were recovered by filtration. Yield: 31.3 g.

m. p.: 263° C. (dec.)

¹H-NMR (DMSO-d₆) δ (ppm) 6.32 (1H, d, J=16 Hz) 7.46~7.58(5H, m) 7.49(1H, d, J=16 Hz) 8.26(1H, bs)

PREPARATIVE EXAMPLES 13 to 16

The following compounds were each prepared in a similar manner to that of the Preparative Example 12.

PREPARATIVE EXAMPLE 13

(E)-{3-(3-Fluorophenyl)-1H-pyrazol-4-yl}-2-propenoic acid

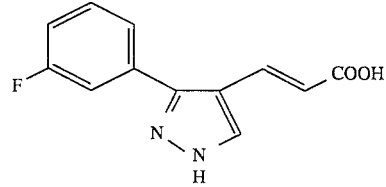

m.p.: 281° C. (approx. dec.)

¹H-NMR (DMSO-d₆) δ (ppm) 6.33(1H, d, J=16 Hz) 7.26~7.39(3H, m) 7.49(1H, d, J=16 Hz) 7.59(1H, m) 8.33(1H, br-s)

This compound could also be prepared by the following process.

A liquid mixture comprising 3-(3-fluorophenyl)-1 H-pyrazole-4-carbaldehyde (2 g, 10.5 mmol), ethyl diethylphosphonoacetate (3.25 g, 14.5 mmol), a methanolic solution of sodium methylate (28%, 2.6 g, 12.0 mmol) and tetrahydrofuran (20 ml) was stirred in a 50-ml flask at room temperature for 24 hours to complete a reaction. 50 ml of a 1N aqueous solution of caustic soda was added to the reaction mixture. The obtained mixture was stirred for 36 hours and neutralized with a 1N aqueous solution of hydrochloric acid. Water (50 ml) was added to the resulting mixture to form precipitates, which were recovered by filtration, washed with water, well dried, and added to acetone (15 ml). The obtained mixture was stirred for one hour, followed by the addition thereto of isopropyl ether (15 ml). The crystals thus precipitated were recovered by filtration. 1.89 g of the title compound was obtained (yield: 79%).

PREPARATIVE EXAMPLE 14

(E)-{3-(5-Methylthiophen-2-yl)-1H-pyrazol-4-yl}-2-propenoic acid

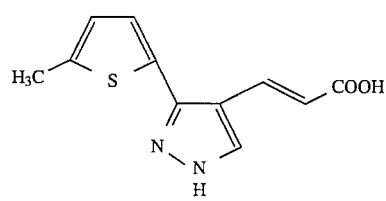

m.p.: 228° C. (approx. dec.)

¹H-NMR (DMSO-d₆) δ (ppm) 2.50(3H, s) 6.33(1H, d, J=16 Hz) 6.90(1H, br-s) 7.12(1H, br-s) 7.64(1H, d, J=16 Hz) 8.27(1H, br-s)

PREPARATIVE EXAMPLE 15

(E)-2-Methyl-{3-(5-methylfuran-2-yl)-1H-pyrazol-4-yl}-2-propenoic acid

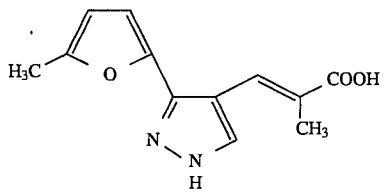

m.p.: 215°~218° C.
$^1$H-NMR (DMSO-d$_6$) δ (ppm) 2.02(8H, s) 2.35(3H, s) 6.26(1H, d, J=3 Hz) 6.57(1H, d, J=3 Hz) 7.79(1H, s) 8.01(1H, br-s)

PREPARATIVE EXAMPLE 16

(E)-3-{3-(5-Chlorothiophen-2-yl)-1H-pyrazol-4-yl}-2-propenoic acid

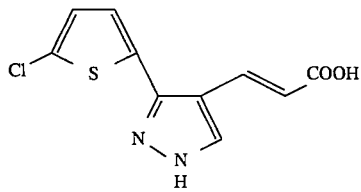

$^1$H-NMR (DMSO-d$_6$) δ (ppm) 6.37(1H, d, J=16 Hz) 7.18(1H, d, J=4 Hz) 7.21(1H, d, J=4 Hz) 7.60(1H, d, J=16 Hz) 8.39(1H, s)

PREPARATIVE EXAMPLE 17

{1-(4-Chloropyridin-2-yl)-2-(pyridin-2-yl)}ethyl alcohol

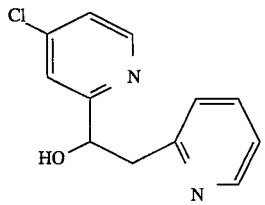

21.1 g of α-picoline was dissolved in 500 ml of tetrahydrofuran and the obtained solution was cooled to −60° to −55° C. 99.6 ml of a 2.5M solution of n-butyllithium in hexane was dropped into the resulting solution in such a way that the bulk temperature did not exceed −55° C. After the completion of the dropping, the obtained mixture was stirred for 20 minutes. A solution of 32.0 g of 4-chloro-2-pyridinecarbaldehyde in tetrahydrofuran was dropped into the resulting mixture in such a way that the bulk temperature did not exceed −55° C. The cooling bath was taken off and the mixture was stirred for 20 minutes, followed by the addition thereto of water. The resulting mixture was extracted with ethyl acetate. The organic phase was dried over sodium sulfate and distilled in a vacuum to remove the solvent. The residue was purified by silica gel column chromatography (with an ethyl acetate/hexane (2:1) mixture) to give 21.9 g of the title compound as an oil.

NMR (CDCl$_3$) δ (ppm) 3.13 (1H, dd, J=9 Hz 15 Hz) 3.39(1H, dd, J=3 Hz, 15 Hz) 5.20(1H, dd, J=3 Hz, 9 Hz) 6.34(1H, br-s) 7.15~7.21(3H, m) 8.44(1H, d, J=6 Hz) 8.52(1H, ddd, J=1, 2, 5 Hz)

PREPARATIVE EXAMPLE 18

1-(3-Chlorophenyl)-2-(1-triphenylmethylimidazol-2-yl)ethyl alcohol

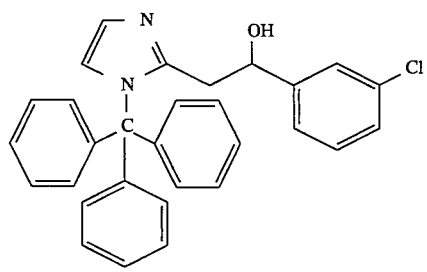

The title compound was prepared in a similar manner to that of the Preparative Example 17.

$^1$H-NMR (CDCl$_3$) δ (ppm) 2.20 (1H, dd, J=3 Hz, 16 Hz) 2.28 (1H, dd, J=10 Hz, 16 Hz) 4.20 (1H, dd, J=3 Hz, 10 Hz) 6.73 (1H, d, J=2 Hz) 6.82~6.85(2H, m) 6.98(1H, d, J=2 Hz) 7.06~7.10(8H, m) 7.30~7.35(9H, m)

PREPARATIVE EXAMPLE 19

1-(3-Chlorophenyl)-2-(pyridin-2-yl)ethyl alcohol

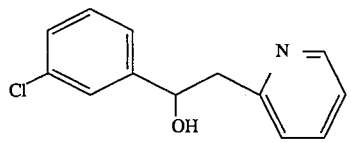

50 ml of a solution of 5.58 g of 2-picoline in tetrahydrofuran was cooled to −65° C., followed by the dropwise addition thereto of 26.4 ml of a 2.5M solution of n-butyllithium in hexane. The obtained mixture was stirred at a bulk temperature of −50° to −30° C. for 30 minutes, followed by the dropwise addition thereto of 50 ml of a tetrahydrofuran solution of 8.85 g of 3-chlorobenzaldehyde at −50° C. The temperature of the obtained mixture was raised to 0° C. The resulting mixture was cooled, treated with an aqueous solution of ammonium chloride, and extracted with ethyl acetate. The organic phase was dried over anhydrous magnesium sulfate and concentrated (yield: 13.5 g). This concentrate was used in the subsequent step without purification.

$^1$H-NMR (CDCl$_3$) δ (ppm) 3.11(3H, d, J=6 Hz) 5.15(2H, t, J=6 Hz) 7.11(1H, d, J=8 Hz) 7.17~7.33 (m, 4 H) 7.44(1H, d, J=2 Hz) 7.64(1H, m) 8.54(1H, d, J=5 Hz)

PREPARATIVE EXAMPLE 20

1-(6-Chloropyridin-2-yl)-2-(pyridin-2-yl)ethyl alcohol

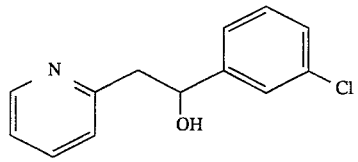

50.2 g of 2-picoline was dissolved in 1363 ml of tetrahydrofuran and 237.2 ml of a 2.5M solution of n-butyllithium in hexane was added to the obtained solution at −50° C. in a nitrogen stream. The obtained mixture was stirred at that temperature for 50 minutes, followed by the addition thereto of a solution of 76.2 g of 6-chloro-2-pyridinecarbaldehyde in 1363 ml of tetrahydrofuran at −50° C. The obtained mixture was stirred at that temperature for 30 minutes and brought to 0° C. at room temperature. Water was added to the resulting mixture to terminate the reaction. Ethyl acetate and water were added to the obtained mixture to conduct extraction. The ethyl acetate phase was washed with a saturated aqueous solution of common salt, dried over anhydrous sodium sulfate, and concentrated. The residue was purified by silica gel chromatography (with a hexane/ethyl acetate (2:1) mixture) to give 38.7 g of the title compound.

$^1$H-NMR (CDCl$_3$) δ (ppm) 3.12(1H, dd, J=9 Hz, 15 Hz) 3.40 (1H, dd, J=3 Hz, 15 Hz) 5.19(1H, dd, J=3 Hz, 9 Hz) 6.37(1H, br-s) 7.15~7.20(3H, m) 7.51~7.66(3H, m) 8.50(1H, ddd, J=1 Hz, 2 Hz, 5 Hz)

PREPARATIVE EXAMPLE 21

N-[{1-(4-chloropyridin-2-yl)-2-(pyridin-2-yl)}ethyl]-phthalimide

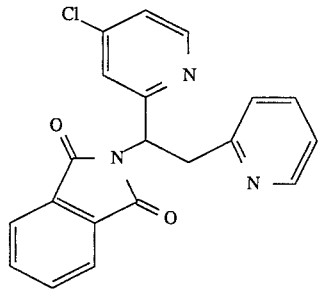

21.9 g of {1-(4-chloropyridin-2-yl)-2-(pyridin-2yl)}ethyl alcohol, 27.1 g of triphenylphosphine and 15.2 g of phthalimide were dissolved in 200 ml of tetrahydrofuran. The obtained solution was cooled to −20° C., followed by the dropwise addition thereto of a tetrahydrofuran solution of 18.0 g of diethyl azodicarboxylate. After the completion of the dropwise addition, the mixture was brought to room temperature and stirred for 20 minutes.

Aqueous hydrochloric acid was added to the resulting mixture and the obtained mixture was washed with ethyl acetate, followed by the neutralization of the aqueous hydrochloric acid with sodium hydrogen-carbonate. The resulting mixture was extracted with ethyl acetate. The organic phase was dried over sodium sulfate and heated to distill away the solvent. The residue was purified by silica gel chromatography (with a hexane/ethyl acetate (3:1 to 1:1) mixture) to give 23.4 g of the title compound as a crystal (yield: 68.8%.

PREPARATIVE EXAMPLE 22

N-{1-(3-Chlorophenyl)-2-(Pyridin-2-yl)ethyl}-phthalimide

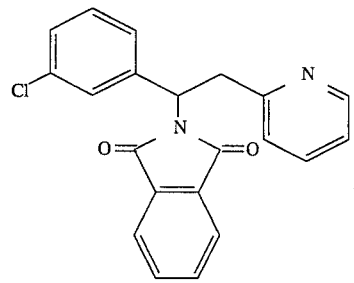

70 ml of a solution of 16.5 g of triphenylphosphine in tetrahydrofuran was cooled to −50° C., followed by the gradual dropwise addition thereto of 40 ml of a solution of 11.0 g of diethyl azodicarboxylate in tetrahydrofuran. The obtained mixture was stirred at −30° C. for 30 minutes, followed by the dropwise addition thereto of 50 ml of a tetrahydrofuran solution of 13.4 g of the 1-(3-chlorophenyl)-2-(pyridin-2-yl)ethyl alcohol prepared in the Preparative Example 19. The obtained mixture was stirred at that temperature for 30 minutes, followed by the addition thereto of 9.28 g of phthalimide. The obtained mixture was stirred at room temperature for 30 minutes and extracted with ethyl acetate. The organic phase was dried over anhydrous magnesium sulfate and concentrated. The residue was subjected to column chromatography and eluted with a toluene/ethyl acetate mixture. Yield: 12.9 g.

$^1$H-NMR (CDCl$_3$) δ (ppm) 3.64(1H, dd, J=6 Hz, 14 Hz) 4.14(1H, dd, J=11 Hz, 14 Hz) 5.95(1H, dd, J=6 Hz, 11 Hz) 7.05(1H, m) 7.14(1H, d, J=8 Hz) 7.22~7.29(2H, m) 7.47~7.53(2H, m) 7.60(1H, d, J=2 Hz) 7.63~7.68(2H, m) 7.73~7.78(2H, m) 8.48(1H, d, J=5 Hz)

PREPARATIVE EXAMPLE 23

N-{1-(6-Chloropyridin-2-yl)-2-(pyridin-2-yl)ethyl}-phthalimide

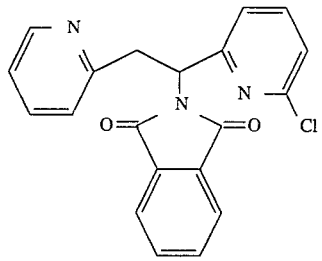

38.6 g of the 1-(6-chloropyridin-2-yl)-2-(pyridin-2-yl)-ethyl alcohol prepared in the Preparative Example 20, 47.8 g of triphenylphosphine and 26.8 g of phthalimide were dissolved in 500 ml of tetrahydrofuran, followed by the addition thereto of 31.7 g of diethyl azodicarboxylate. The obtained mixture was stirred at room temperature overnight and concentrated, followed by the addition thereto of diethyl ether. The obtained mixture was filtered to remove insolubles and the filtrate was purified by silica gel chromatography (with a hexane/ethyl acetate (2:1) mixture) to give 77.1 g of the title compound as a roughly purified product.

$^1$H-NMR (CDCl$_3$) δ (ppm) 3.92(1H, dd, J=6 Hz, 14 Hz) 4.00(1H, dd, J=11 Hz, 14 Hz) 6.04(1H, dd, J=6 Hz, 11 Hz) 7.04(1H, ddd, J=1, 5, 6 Hz) 7.22(1H, d, J=8 Hz) 7.33(1H, d, J=8 Hz) 7.44~7.80(7H, m) 8.41(1H, ddd, J=1, 2, 5 Hz)

PREPARATIVE EXAMPLE 24

1-(6-Chloropyridin-2-yl)-2-(pyridin-2-yl)ethylamine

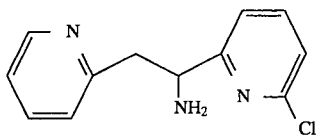

1 l of methanol was mixed with 77 g of the crude N-{1-(6-chloropyridin-2-yl)-2-(pyridin-2-yl)ethyl}-phthalimide prepared in the Preparative Example 23 and 16.5 g of hydrazine monohydrate. The obtained mixture was heated under reflux for 2 hours to conduct a reaction. After the reaction mixture was allowed to stand at room temperature, the precipitated crystals were filtered out and the filtrate was concentrated. Water and ethyl acetate were added to the concentrate to conduct extraction. The organic phase was washed with a saturated aqueous solution of common salt, dried over anhydrous sodium sulfate, and concentrated. The residue was purified by silica gel chromatography (with a methanol/dichloromethane (5:95 mixture) to give 22.38 g of the title compound.

$^1$H-NMR (CDCl$_3$) δ (ppm) 3.09(1H, dd, J=9 Hz, 14 Hz) 3.26(1H, dd, J=5 Hz, 14 Hz) 4.48(1H, dd, J=5 Hz, 9 Hz) 7.09(1H, d, JK=8 Hz) 7.13(1H, ddd, J=1 Hz, 5 Hz, 8 Hz) 7.19(1H, t, J=8 Hz) 7.20(1H, t, J=8 Hz) 7.56(1H, t, J=8 Hz) 7.57(1H, td, J=8, 2 Hz) 8.56(1H, ddd, J=1, 2, 5 Hz)

PREPARATIVE EXAMPLE 25

1-(8-Chlorophenyl)-2-(1-triphenylmethylimidazol-2-yl)ethylamine

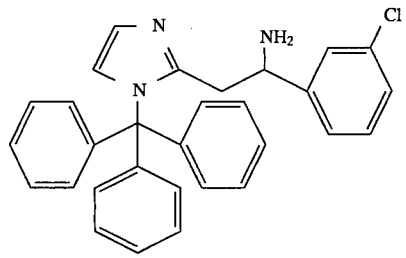

The title compound was prepared in a similar manner to that of the Preparative Example 24.

$^1$H-NMR (CDCl$_3$) δ (ppm) 2.19(2H, d, J=7 Hz) 3.94(1H, t, J=7 Hz) 6.75(1H, d, J=2 Hz) 6.83~6.86(1H, m) 6.90~6.93(1H, m) 6.99(1H, d, J=2 Hz) 7.03~7.13(8H, m) 7.25~7.36(9H, m)

PREPARATIVE EXAMPLE 26

{1-(4-Caloropyridin-2-yl)-2-(pyridin-2yl)}ethylamine

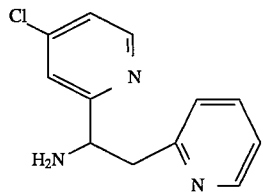

99 g of the N-[{1-(4-chloropyridin-2-yl)-2-(pyridin-2-yl)}ethyl]phthalimide prepared in the Preparative Example 21 was dissolved in 1 l of ethanol, followed by the addition thereto of 41 ml of hydrazine monohydrate. The obtained mixture was refluxed for one hour. The precipitated white solid was filtered out and the filtrate was subjected to vacuum stripping. The residue was filtered to remove insolubles. The filtrate was purified by silica gel chromatography (with a chloroform/methanol (20:1) mixture) to give 38.6 g of the title compound as an oil.

$^1$H-NMR (CDCl$_3$) δ (ppm) 2.26(2H, br-s) 3.07(1H, dd, J=9, 14 Hz) 3.28(1H, dd, J=5, 14 Hz) 4.50 (1H, dd, J=5, 9 Hz) 7.08 (1H, d, J=8 Hz) 7.14(1H, ddd, J=1, 5, 8 Hz) 7.17(1H, dd, J=2, 5 Hz) 7.34 (1H, d, J=2 Hz) 7.57 (1H, td, J=8, 2 Hz) 8.47(1H, d, J=6 Hz) 8.57(1H, ddd, J=1, 2, 5 Hz)

PREPARATIVE EXAMPLE 27

{1-(4-Chloropyridin-2-yl)-2-(pyridin-2-yl)}ethylamine

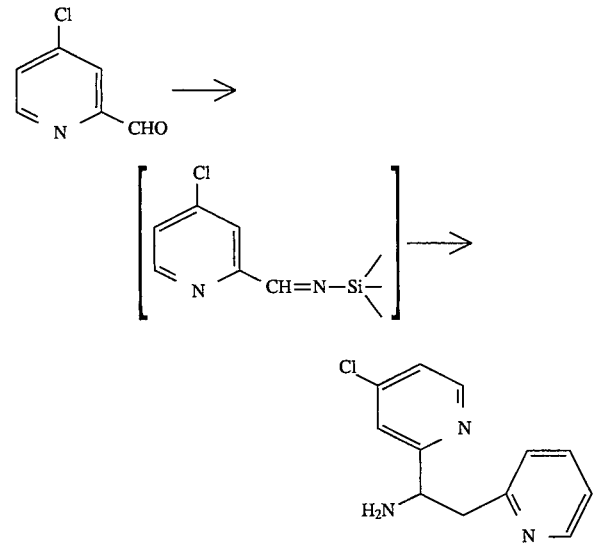

A solution of 2.5 g (15.5 mmol) of 1,1,1,3,3,3-hexamethyldisilazane in 6 ml of tetrahydrofuran was cooled to −20° C. 9.4 ml (15.5 mmol) of a 1.65M solution of n-butyllithium in n-hexane was dropped into the resulting solution for 3 minutes in such a way that the temperature did not exceed −15° C. The obtained mixture was stirred at −20° C. for 15 minutes. A solution of 2.0 g (14.1 mmol) of 4-chloro-2-pyridylaldehyde in 6 ml of tetrahydrofuran was dropped into the resulting mixture for 3 minutes in such a way that the temperature did not exceed −15° C. The temperature of the mixture was raised to −10° C. The resulting mixture was stirred for 15 minutes to give 2-(methyl-N-trimethylsilanylimino)-4-chloropyridine.

(2)

A solution of 1.6 g (17.2 mmol) of α-picoline in 60 ml of tetrahydrofuran was cooled to −65° C. 10.3 ml (17.0 mmol) of a 1.65M solution of n-butyllithium in n-hexane was dropped into the solution for 3 minutes in such a way that the temperature did not exceed −55° C. The obtained solution was stirred at −65° C. for 45 minutes.

The 2-(methyl-N-trimethylsilanylimino)-4-chloropyridine prepared in the step (1) was dropped into the resulting solution for two minutes in such a way that the temperature did not exceed −60° C. The obtained mixture was stirred at −65° C. for 15 minutes, diluted with 100 ml of a saturated aqueous solution of ammonium chloride, and extracted with 100 ml of ethyl acetate twice. The combined organic phases were dried over sodium sulfate and evaporated in a vacuum to dryness to give the title compound as a crude product. This crude product was purified by silica gel column chromatography (with a methanol/dichloromethane system) to give the title compound as a green oil.

PREPARATIVE EXAMPLE 28

1-(3-Chlorophenyl)-2-(pyridin-2-yl)ethylamine

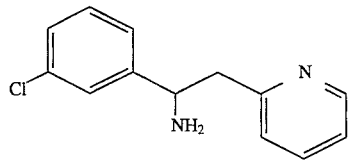

150 ml of a solution of 5.25 g of hydrazine hydrate in ethanol was added to 12.7 g of the N-{1-(3-chlorophenyl)-2-(pyridin-2-yl)ethyl}phthalimide prepared in the Preparative Example 22. The obtained mixture was heated under reflux for 2 hours. The precipitated crystals were filtered out and the filtrate was concentrated, followed by the addition thereto of ethyl acetate. The precipitated impurities were filtered out and the filtrate was concentrated to give the title compound. Yield: 7.9 g.

$^1$H-NMR (CDCl$_3$) δ (ppm) 3.01(1H, dd, J=9 Hz, 14 Hz) 3.11(1H, dd, J=5 Hz, 14 Hz) 4.48(1H, dd, J=5 Hz, 9 Hz) 7.05(1H, d, J=8 Hz) 7.15(1H, ddd, J=2 Hz, 5 Hz, 8 Hz) 7.18~7.27(3H, m) 7.41(1H, d, J=2 Hz) 7.58(1H, td, J=2 Hz, 8 Hz) 8.58(1H, d, J=5 Hz)

PREPARATIVE EXAMPLE 29

(−)-N-{1-(2,5-Difluorophenyl)-2-(pyridin-2-yl)}-ethylamine

A mixture comprising 36 g of {1-(2,5-difluorophenyl)-2-(pyridin-2-yl)}ethylamine, 25.73 g of R-(−)-mandelic acid, 32.43 g of 1-(3-dimethylaminopropyl)-3-ethylcarbodiimide hydrochloride, 22.86 g of 1-hydroxybenzotriazole, 23.57 mg of triethylamine and 500 ml of tetrahydrofuran was heated under reflux for 45 minutes and cooled by allowing to stand, followed by the addition thereto of a saturated aqueous solution of sodium hydrogencarbonate and water in this order. The obtained mixture was extracted with chloroform. The organic phase was dried over anhydrous magnesium sulfate and distilled in a vacuum to remove the solvent. The residue was subjected to silica gel chromatography and then to gradient elution with a chloroform/isopropyl alcohol (100:1 (v/v) to 50:1 (v/v)) mixture to recover the first eluted diastereomer, which was recrystallized from ethyl acetate/hexane to give 24.3 g of pure crystals. The crystals were added to 6N hydrochloric acid and the obtained mixture was heated under reflux for 2 hours, basified with a 1N aqueous solution of sodium hydroxide, and extracted with ethyl acetate. The organic phase was washed with water, dried over anhydrous magnesium sulfate, and distilled in a vacuum to remove the solvent. Thus 13.1 g of the title compound was obtained.

$[\alpha]_D^{20}$=55.9° (c=1, methanol)

$^1$H-NMR (CDCl$_3$) δ (ppm) 3.03(1H, dd, J=14, 9 Hz) 3.20(1H, dd, J=14, 5 Hz) 4.72(1H, dd, J=9, 5 Hz) 6.85~6.91(1H, m) 6.94~7.00(1H, m) 7.09(1H, d, J=8 Hz) 7.13~7.21(2H, m) 7.58(1H, dr, J=8, 2 Hz) 8.57(1H, ddd, J=5, 2, 1 Hz)

(+)-N-{1-(2,5-Difluorophenyl)-2-(pyridin-2-yl)}-ethylamine $[\alpha]_D^{20}$=+55.9° (c=1, methanol)

PREPARATIVE EXAMPLE 30

(−)-1-(6-Chloropyridin-2-yl)-2-(pyridin-2-yl)ethylamine

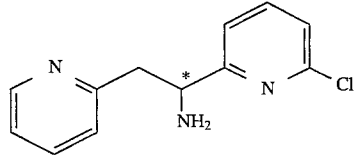

Tetrahydrofuran (1000 ml) was mixed with 22.4 g of (±)-1-(6-chloropyridin-2-yl)-2-(pyridin-2-yl)ethylamine, 14.6 g of (R)-(−)-mandelic acid, 20.3 g of 1-(3-dimethylaminopropyl)-3-ethylcarbodiimide hydrochloride, 16.1 g of 1-hydroxybenzotriazole and 16.6 ml of triethylamine. The obtained mixture was heated under reflux for one hour and the reaction mixture was concentrated, washed with water and a saturated aqueous solution of common salt, dried over anhydrous sodium sulfate, concentrated, and purified by silica gel chromatography (with an isopropyl alcohol/chloroform (1:99) mixture). 15.2 g of the objective amine diastereomer was recovered as the first eluted fraction. 300 ml of 6N aqueous hydrochloric acid was added to the diastereomer (15.2 g). The obtained mixture was heated under reflux for 1.5 hours to conduct hydrolysis. The reaction mixture was cooled by allowing to stand, adjusted to pH13 with a dilute aqueous solution of sodium hydroxide, and extracted with ethyl acetate. The organic phase was washed with a saturated aqueous solution of common salt, dried over anhydrous sodium sulfate, and concentrated to give 8.9 g of the title compound.

$^1$H-NMR (CDCl$_3$) δ (ppm) 3.09(1H, dd, J=9 Hz, 14 Hz) 3.26(1H, dd, J=5 Hz, 14 Hz) 4.48(1H, dd, J=5 Hz, 9 Hz) 7.09(1H, d, J=8 Hz) 7.13(1H, ddd, J=1 Hz, 5 Hz, 8 Hz) 7.19(1H, t, J=8 Hz) 7.20(1H, t, J=8 Hz) 7.56(1H, t, J=8 HZ) 7.57(1H, td, J=2 Hz, 8 Hz) 8.56(1H, ddd, J=1 Hz, 2 Hz, 5 Hz)

PREPARATIVE EXAMPLE 31

(−)-1-(3-Chlorophenyl)-2-(pyridin-2-yl)ethylamine

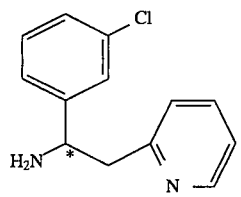

35.9 g of the 1-(3-chlorophenyl)-2-(pyridin-2-yl)ethylamine prepared in the Preparative Example 28 and 23.2 g of D-tartaric acid were dissolved in a mixture comprising 500 ml of ethanol and 100 ml of water at 90° C. The obtained solution was brought to room temperature and the precipitated crystals were recovered by filtration. The wet crystals thus obtained were dissolved in a mixture comprising 300 ml of ethanol and 60 ml of water at 90° C. and the obtained solution was brought to room temperature. The crystals thus precipitated were recovered by filtration and suspended in an aqueous solution of sodium hydroxide. The obtained suspension was extracted with toluene. The toluene phase was dried over magnesium sulfate and distilled in a vacuum to remove the solvent, thus giving 7.7 g of the title compound as a pale-yellow oil. The optical purity of this product was determined by high-performance liquid chromatography (with a hexane/isopropanol (8:1) mixture containing 0.1% of diethylamine) (>97%ee).

$[\alpha]_D^{20}$=−78.9° (c=0.598, methanol)

$^1$H-NMR (CDCl$_3$) δ (ppm) 3.01(1H, dd, J=9 Hz, 14 Hz) 3.12(1H, dd, J=5 Hz, 14 Hz) 4.49(1H, dd, J=5 Hz, 9 Hz) 7.15(1H, dd, J=5 Hz, 8 Hz) 7.19~7.28(3H, m) 7.41(1H, s) 7.58(1H, td, J=2 Hz, 8 Hz) 7.60(1H, d, J=8 Hz) 8.59(1H, d, J=5 Hz)

PREPARATIVE EXAMPLE 32

(−)-{1-(4-Chloropyridin-2-yl)-2-(pyridin-2-yl)}-ethylamine

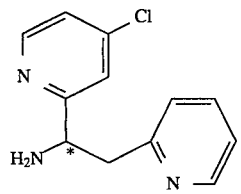

The title compound was prepared in a similar manner to that of the Preparative Example 30.

$^1$H-NMR (CDCl$_3$) δ (ppm) 3.07(1H, dd, J=9 Hz, 14 Hz) 3.28(1H, dd, J=5 Hz, 14 Hz) 4.50(1H, dd, J=5 Hz, 9 Hz) 7.08(1H, d, J=8 Hz) 7.14(1H, dd, J=5 Hz, 5 Hz) 7.17(1H, d, J=5 Hz) 7.34(1H, s) 7.57(1H, dd, J=5 Hz, 5 Hz) 8.47(1 Hz, d, J=8 Hz) 8.57(1H, J=5 Hz)

$[\alpha]_D^{20}$=−55.4° (c=0.386, methanol)

(+)-{1-(4-Chloropyridin-2-yl)-2-(pyridin-2-yl)}-ethylamine $[\alpha]_D^{20}$=+55.4 (c=0.386, methanol)

PREPARATION EXAMPLE 33

4-Phenyl-1H-imidazole-5-carbaldehyde

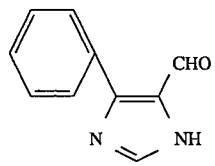

1,4-Dioxane (10 ml) was mixed with 1 g of (4-phenyl-1H-imidazol-5-yl)methyl alcohol and 3 g of activated manganese dioxide. The obtained mixture was treated at 80° C. for 30 minutes to conduct a reaction. The reaction mixture was passed through a hot filter and the filter cake was washed with acetone. The washings and the filtrate were combined and concentrated to give 0.7 g of the title compound.

$^1$H-NMR (DMSO-d$_6$) δ (ppm) 7.42~7.52(3H, m) 7.81~7.84(2H, m) 8.03(1H, s) 9.87(1H, s)

PREPARATION EXAMPLE 34

(E)-3-(4-Phenyl-1H-imidazol-5-yl)-2-propenoic acid hydrochloride

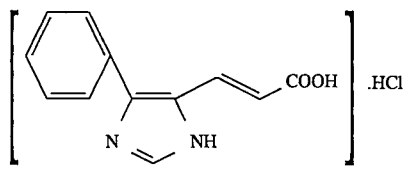

17.7 g of a 554 oily dispersion of sodium hydride was suspended in 500 ml of tetrahydrofuran, followed by the gradual addition thereto of a solution of 95 g of ethyl diethylphosplonoacetate in 200 ml of tetrahydrofuran. The obtained mixture was stirred as such at room temperature for 30 minutes, followed by the addition thereto of a solution of 63.6 g of 4-phenyl-1H-imidazole-5-carbaldehyde in 500 ml of tetrahydrofuran. The obtained mixture was stirred at room temperature overnight and concentrated, and water and ethyl acetate were added to the concentrate to conduct extraction. The organic phase was washed with a saturated aqueous solution of common salt, dried over anhydrous sodium sulfate, and concentrated. The residue was purified by silica gel chromatography. Two main products were isolated by elution with a methanol/dichloromethane (2:98) mixture. Between the products, the first eluted one was ethyl ester of the objective compound. 21.5 g of the ester was obtained as a crude product.

This crude product was dissolved in a mixture comprising 200 ml of methanol and a 2N aqueous solution of sodium hydroxide. The obtained solution was heated under reflux for one hour to conduct hydrolysis. The reaction mixture was concentrated, and water and dichloromethane were added to the concentrate to conduct extraction. The aqueous phase was washed with dichloromethane and adjusted to pH2 to 3 with hydrochloric acid. The precipitated crystals were recovered by filtration, washed with water, and dried to give 13.5 g of the title compound.

MS m/z: 215 (MH$^+$)

$^1$H-NMR (DMSO-d$_6$) δ (ppm) 6.15(1H, d, J=13 Hz) 6.97(1H, d, J=13 Hz) 7.53~7.67(5H, m) 9.13(1H, s)

PREPARATION EXAMPLE 35

(Z)-3-(4-Phenyl-1H-imidazol-5-yl)-2-propenoic acid hydrochloride

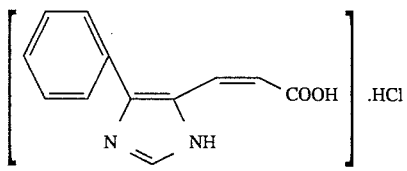

76.5 g of ethyl (Z)-3-(4-phenyl-1H-imidazol-5-yl)-2-propenoate was obtained as another fraction of the silica gel chromatography conducted in the Example 29. This ester was dissolved in a mixture comprising 500 ml of methanol and a 2N aqueous solution of sodium hydroxide. The obtained solution was heated under reflux for one hour to conduct hydrolysis. The reaction mixture was concentrated, and water and dichloromethane were added to the concentrate to conduct extraction. The aqueous phase was washed with dichloromethane and adjusted to pH4 with hydrochloric acid. The precipitated crystals were recovered by filtration, washed with water, and dried to give 51.3 g of the title compound.

MS m/z: 215 (MH$^+$)

$^1$H-NMR (DMSO-d$_6$) δ (ppm) 6.90(1H, d, J=16 Hz) 7.40(1H, d, J=16 Hz) 7.54~7.65(6H, m) 9.40(1H, s)

PREPARATION EXAMPLE 36

{1-(4-Chloropyridin-2-yl)-2-(pyridin-2-yl)}ethanone

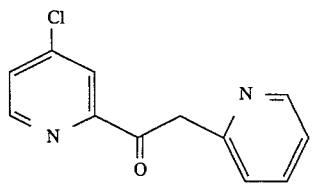

A solution of 1 g (11 mmol) of picoline in tetrahydrofuran (20 ml) was cooled to −78° C. 6.4 ml (11 mmol) of a 1.6M solution of n-butyllithium in hexane was dropped into the solution, while the mixture was kept at a temperature of −60° C. or below. After the completion of the dropping, the resulting mixture was stirred at that temperature for 30 minutes, followed by the addition thereto of a solution of 1.84 g (11 mmol) of methyl 4-chloropicolinate in 40 ml of tetrahydrofuran which had been cooled to −40° C. The obtained mixture was stirred at that temperature for 30 minutes and brought to room temperature, followed by the addition thereto of 200 ml of ethyl acetate and 200 ml of water. The resulting mixture was neutralized with an aqueous solution of sodium hydrogencarbonate. The ethyl acetate phase was recovered, washed with water and an aqueous solution of common salt, dried over magnesium sulfate, and concentrated to give the title compound.

$^1$H-NMR (CDCl$_3$) keto form: enol form=1:10 keto form: δ (ppm) 4.70(10H, s) 7.17~7.34(10H, m) 7.48(10H, d, J=6 Hz) 8.06(10H, s) 8.52~8.60(10H, m)

enol form: δ (ppm) 6.81(10H, s) 7.61(10H, dd, J=5, 6 Hz) 7.20(10H, d, J=6 Hz) 7.27(10H, d, J=5 Hz) 7.67 (10H, dd, J=5, 6 Hz) 7.98 (10H, s ) 8.35(1H, d, J=5 Hz) 8.51 (1H, d, J=5 Hz)

MS m/z: 233 (MH$^+$)

PREPARATION EXAMPLE 37

{1-(4-Chloropyridin-2-yl)-2-(pyridin-2-yl)}ethanone oxime

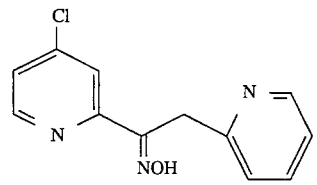

50 ml of a methanolic solution of 1.4 g (22 mmol) of hydroxylamine hydrochloride and 1.8 g (22 mmol) of sodium hydrogencarbonate was added to the 1-(4-chloro-2-pyridyl)-2-(2-pyridyl)ethanone prepared in the Example 31. The obtained mixture was stirred at room temperature for hours and concentrated in a vacuum, followed by the addition thereto of 300 ml of ethyl acetate and 200 ml of water. The resulting aqueous phase was adjusted to pH7 to recover the organic phase. The organic phase was washed with water and an aqueous solution of common salt, dried over magnesium sulfate, and concentrated in a vacuum. Acetone (20 ml) was added to the residue, and the precipitated crystals were recovered by filtration. 1.77 g of the title compound was obtained. Yield: 67%.

m.p.: 162°~3° C.

MS m/z: 248 (MH$^+$)

elemental analysis as $C_{12}H_{10}ClN_3O$

|  | C | H | N |
| --- | --- | --- | --- |
| calcd.: | 58.19 | 4.07 | 16.97% |
| found: | 58.29 | 4.10 | 16.83% |

$^1$H-NMR (CD30D) δ (ppm) 4.70(2H, s) 7.17~7.24(2H, m) 7.35(1H, d, J=6 Hz) 7.66(1H, dd, J=6, 6 Hz) 8.00(1H, s) 8.34(1H, d, J=5 Hz) 8.42(1H, d, J=5 Hz)

PREPARATION EXAMPLE 38

{1-(4-Chloropyridin-2-yl)-2-(pyridin-2-yl)}ethylamine

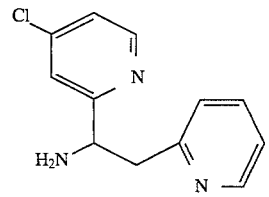

15 g (60.6 mmol) of the 1-(4-chloro-2-pyridyl)-2-2-pyridyl)ethanone oxime prepared in the Example 32 was dissolves in 120 ml of trifluoroacetic acid, followed by the addition thereto of 22 g of powdered zinc in several portions. After the completion of the addition, the reaction mixture was added to a mixture comprising 900 ml of a 2N aqueous solution of sodium hydroxide and 500 ml of dichloromethane under cooling with ice. The organic phase was recovered, washed with water and an aqueous solution of common salt, dried over magnesium sulfate, and concentrated in a vacuum to give 13.47 g of the title compound. Yield: 96%.

EXAMPLE 1

(+)-(E)-N-{1-(3-Chlorophenyl)-2-(Pyridin-2-yl)-ethyl)}-3-(3-1H-phenylpyrazol-4-yl)-2-propenamide

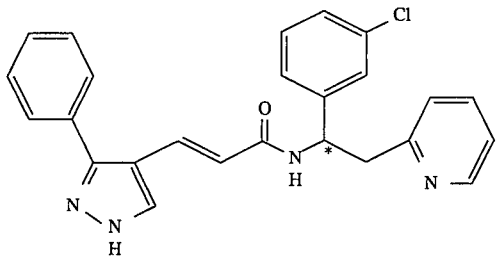

2.93 g of (E)-(3-phenyl-1H-pyrazol-4-yl)-2-propenoic acid, 3.18 g of (−)-1-(3-chlorophenyl)-2-(pyridin-2-yl)ethylamine, 2.76 g of 1-(3-dimethylaminopropyl)-3-ethylcarbodiimide hydrochloride, 1.94 g of 1-hydroxybenzotriazole and 2.01 ml of triethylamine were suspended in tetrahydrofuran. The obtained suspension was stirred at 60° C. for one hour, followed by the addition thereto of water. The obtained mixture was extracted with ethyl acetate and the organic phase was dried over magnesium sulfate. The resulting mixture was freed from the magnesium sulfate by filtration and distilled in a vacuum to remove the solvent. The residue was purified by silica gel chromatography (with a dichloromethine/ethanol (20:1) mixture) to give 5.32 g of the title compound as a pale-yellow amorphous substance.

$[\alpha]_D^{20}$=+76.6° (c=0.483, methanol)

$^1$H-NMR (CDCl$_3$) δ (ppm) 3.18(1H, dd, J=8 Hz, 14 Hz) 3.32(1H, dd, J=5 Hz, 14 Hz) 5.42(1H, m) 8.28(1H, d, J=16 Hz) 7.06(1H, d, J=8 Hz) 7.10~7.24(5H, m) 7.36~7.50(3H, m) 7.44~7.50(2H, m) 7.55(1H, d, J=16 Hz) 7.58(1H, td, J=2 Hz, 8 Hz) 7.80(1H, s) 8.20(1H, d, J=8 Hz) 8.45(1H, d, J=5 Hz)

EXAMPLE 2

(+)-(E)-N-{1-(4-Chloropyridin-2-yl)-2-(pyridin-2-yl)-ethyl}-3-{3-(3-fluorophenyl)-1H-pyrazol-4-yl}-2-propenamide

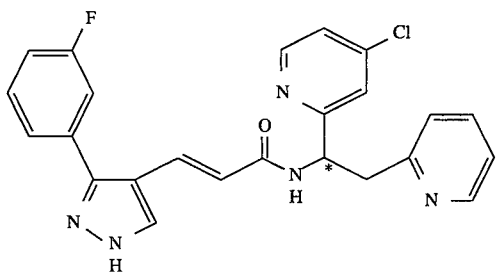

7.1 g of (E)-{3-(S-fluorophenyl)-1H-pyrazol-4-yl}-2-propenoic acid, 6.5 g of (−)-1-(4-chloropyridin-2-yl)-2-(pyridin-2-yl)ethylamine, 5.9 g of 1-(3-dimethylaminopropyl)-3-ethylcarbodiimide hydrochloride, 4.1 g of 1-hydroxybenzotriazole and 4.3 ml of triethylamine were suspended in tetrahydrofuran. The obtained suspension was stirred at 60° C. for one hour, followed by the addition thereto of water. The resulting mixture was extracted with ethyl acetate. The organic phase was dried over magnesium sulfate and the magnesium sulfate was filtered out. The filtrate was distilled in a vacuum to remove the solvent and the residue was purified by silica gel chromatography (with a dichloromethane/ethanol (20:1 to 10:1) mixture). The eluate was distilled in a vacuum to remove the solvent, thus giving a solid. Dichloromethine was added to the solid to form a gel, which was filtered to recover a solid. Dichloromethane was added to this solid to form a gel. This gel was filtered to give 5.22 g of the title compound as a white solid.

$[\alpha]_D^{20}$=+52.5° (c=0.594, methanol)

$^1$H-NMR (CDCl$_3$) δ (ppm) 3.34~3.46(2H, m) 5.55(1H, m) 6.30(1H, d, J=16 Hz) 7.04~7.20(5H, m) 7.20~7.30(2H, m) 7.38(1H, dr, J=6 Hz, 9 Hz) 7.56(1H, d, J=16 Hz) 7.57(1H, dr, J=2 Hz, 8 Hz) 7.83(1H, s) 8.01(1H, d, J=8 Hz) 8.41(1 Hz, d, J=5 Hz) 8.46(1H, d, J=5 Hz)

EXAMPLES 3 TO 16

The title compounds were each prepared in a similar manner to that of the Example 1 or 2.

EXAMPLE 3

(E)-N-(1,2-Diphenylethyl)-3-{3-(thiophen-2-yl)-1H-pyrazol-4-yl}-2-propenamide

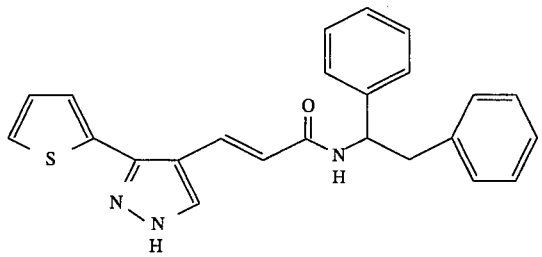

$^1$H-NMR (CDCl$_3$) δ (ppm) 3.08~3.22(2H, m) 5.40(1H, td, J=8 Hz, 8 Hz) 6.14(1H, d, J=16 Hz) 6.76(1H, d, J=8 Hz) 6.86(1H, dd, J=3 Hz, 5 Hz) 7.04~7.28(12H, m) 7.47(1H, s) 7.61(1H, d, J=16 Hz)

EXAMPLE 4

(+)-(E)-N-{1-(4-Chloropyridin-2-yl)-2-(pyridin-2-yl)-ethyl-3-(3-phenyl-1H-pyrazol-4-yl)-2-propenamide

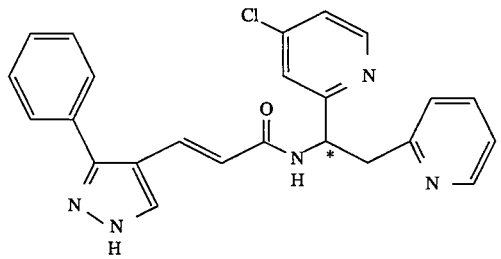

$^1$H-NMR (CDCl$_3$) δ (ppm) 3.37(1H, dd, J=5 Hz, 14 Hz) 3.41(1H, dd, J=7 Hz, 14 Hz) 5.53~5.58(1H, m) 6.33(1H, d, J=16 Hz) 7.10~7.14(3H, m) 7.20(1H, d, J=2 Hz) 7.37~7.42(3H, m) 7.48~7.50(2H, m) 7.56(1H, dt, J=2 Hz, 8 Hz) 7.59(1H, d, J=16 Hz) 7.82(1H, s) 8.13(1H, br) 8.38(1H, d, J=5 Hz) 8.44 (1H, ddd, J=1 Hz, 2 Hz, 5 Hz)

EXAMPLE 5

(+)-(E)-N-{1-(3-Chlorophenyl)-2-(pyridin-2-yl)}ethyl-3-{3-(2-chlorothiophen-5-yl)-1H-pyrazol-4-yl}-2-propenamide

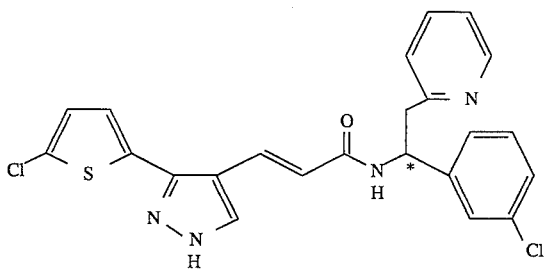

$[\alpha]_D^{20} = +73.4°$ $^1$H-NMR (CDCl$_3$) δ (ppm) 3.18(1H, dd, J=9 Hz, 14 Hz) 3.33(1H, dd, J=4 Hz, 14 Hz) 5.45(1H, m) 6.26(1H, d, J=16 Hz) 6.79(1H, d, J=4 Hz) 6.96 (1H, d, J=4 Hz) 7.12~7.26(6H, m) 7.55~7.63(2H, m) 7.68(1H, s) 8.44(1H, d, J=7 Hz) 8.49 (1H, ddd, J=1 Hz, 2 Hz, 5 Hz)

EXAMPLE 6

(+)-(E)-N-{1-(2,5-Difluorophenyl)-2-(pyridin-2-yl)}-ethyl-3-(3-phenyl-1H-pyrazol-4-yl)-2-propenamide

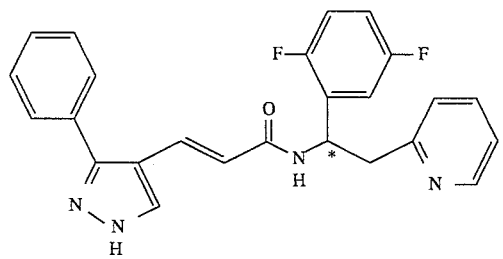

$^1$H-NMR (CDCl$_3$) δ (ppm) 3.22(1H, dd, J=7 Hz, 14 Hz) 3.35(1H, dd, J=5 Hz, 14 Hz) 5.62~5.67(1H, m) 6.35(1H, d, J=16 Hz) 6.95~7.02(2H, m) 7.17(1H, ddd, J=1 Hz, 5 Hz, 8 Hz) 7.40~7.61(7H, m) 7.91(1H, s) 8.02(1H, br-s) 8.50(1H, m)

EXAMPLE 7

(E)-{3-(2-Chlorothiophen-5-yl)-1H-pyrazol-4-yl}-N-{1-(pyridin-2-yl)-2-phenyl}ethyl-2-propenamide hydrochloride

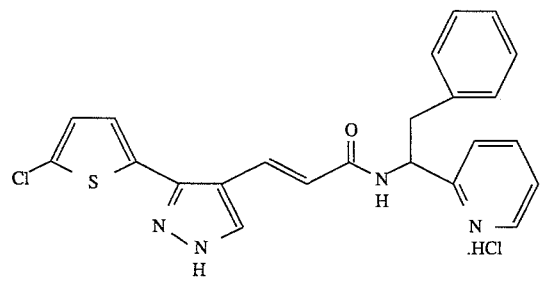

$^1$H-NMR (DMSO-d$_6$) δ (ppm) 3.24(2H, m) 5.50(1H, m) 6.51(1H, d, J=16 Hz) 7.13 (1H, d, J=4 Hz) 7.17 (1H, d, J=4 Hz) 7.20~7.37(5H, m) 7.41(1H, d, J=16 Hz) 7.91(1H, m) 8.03(1H, d, J=8 Hz) 8.17(1H, s) 8.52(1H, m) 8.84 (1H, d, J=6 Hz) 9.23 (1H, m )

EXAMPLE 8

(E)-(3-phenyl-1H-pyrazol-4-yl)-N-{1,2-di(pyridin-2-yl)-ethyl-2-propenamide

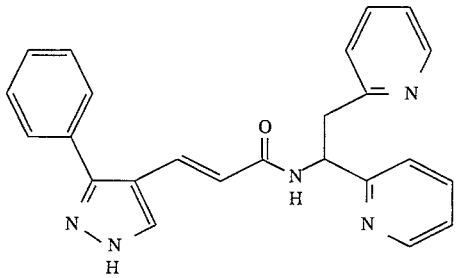

$^1$H-NMR (CDCl$_3$) δ (ppm) 3.37(1H, dd, J=6 Hz, 14 Hz) 3.43(1H, dd, J=8 Hz, 14 Hz) 5.60(1H, m) 6.33(1H, d, J=15 Hz) 7.09~7.14(3H, m) 7.17(1H, d, J=8 Hz) 7.36~7.60(8H, m) 7.82(1H, s) 8.09(1H, d, J=8 Hz) 8.44(1H, dd, J=2 Hz, 5 Hz) 8.48(1H, ddd, J=1 Hz, 2 Hz, 5 Hz)

EXAMPLE 9

(+)-(E)-N-{1-(6-Chloropyridin-2-yl)-2-(pyridin-2-yl)-ethyl-3-{3-(3-fluorophenyl)-1H-pyrazol-4-yl}-2-propenamide

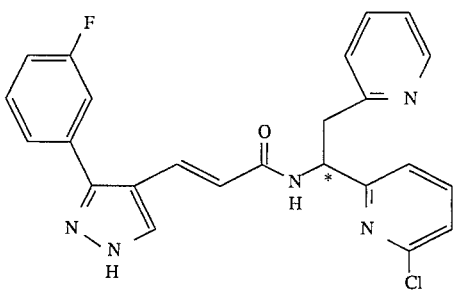

$[\alpha]_D^{20} = +104.3°$ $^1$H-NMR (CDCl$_3$) δ (ppm) 3.37(1H, dd, J=6 Hz, 14 Hz) 3.42 (1H, dd, J=8 Hz, 14 Hz) 5.56(1H, m) 6.29 (1H, d, J=16 Hz) 7.02~7.37(8H, m) 7.49~7.58(2H, m) 7.77(1H, s) 8.01 (1H, d, J=8 Hz) 8.46 (1H, dd, J=2 Hz, 6 Hz)

EXAMPLE 10

(E)-3-{3-(2,5-Dimethylfuran-3-yl)-1H-pyrazol-4-yl}-N-{1-(3-methoxyphenyl-2-(pyridin-2-yl)}ethyl-2-propenamide

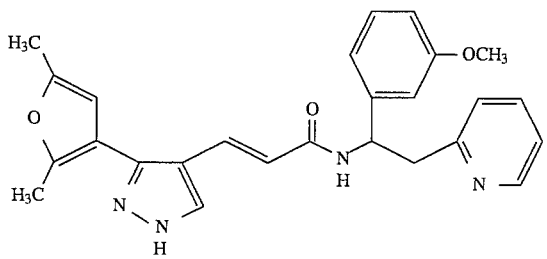

¹H-NMR (CDCl₃) δ (ppm) 2.25(3H, s) 2.26(3H, s) 3.20(1H, dd, J=8 Hz, 14 Hz) 3.34(1H, dd, J=5 Hz, 14 Hz) 3.73(3H, s) 5.42(1H, m) 6.01(1H, s) 6.22(1H, d, J=16 Hz) 6.50~6.78(2H, m) 6.83(1H, d, J=8 Hz) 7.05(1H, d, J=8 Hz) 7.12~7.20(2H, m) 7.40(1H, d, J=16 Hz) 7.56(1H, td, J=2 Hz, 8 Hz) 7.75(1H, d, J=7 Hz) 7.81(1H, s) 8.50(1H, d, J=5 Hz)

EXAMPLE 11

(E)-3-{3-(2-Chlorothiphen-5-yl)-1H-pyrazol-4-yl}-N-{1-(furan-2-yl)-2-phenyl}ethyl-2-propenamide

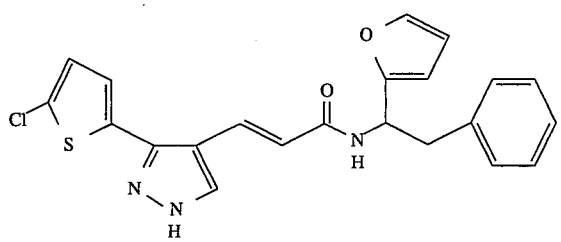

¹H-NMR (DMSO-d₆) δ (ppm) 3.02(1H, dd, J=7 Hz, 14 Hz) 3.13(1H, dd, J=5 Hz, 14 Hz) 5.23(1H, m) 6.23(1H, d, J=3 Hz) 6.32~6.44(2H, m) 7.04~7.26(8H, m) 7.38(1H, d, J=16 Hz) 7.57(1H, s) 8.16(1H, bs) 8.52(1H, d, J=9 Hz)

EXAMPLE 12

(E)-N-(1-Methyl-2-phenyl)ethyl-3-(3-phenyl-1H-pyrazol-4-yl)-2-propenamide

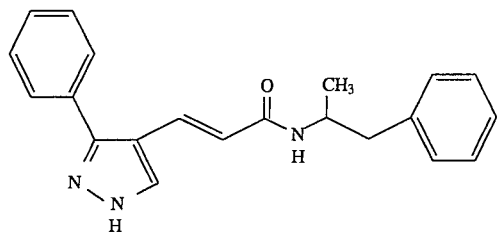

¹H-NMR (DMSO-d₆) δ (ppm) 1.04 (3H, d, J=6 Hz) 2.63 (1H, dd, J=7 Hz, 13 Hz) 2.79 (1H, dd, J=7 Hz, 13 Hz) 4.05(1H, m) 6.35(1H, d, J=16 Hz) 7.14~7.36(6H, m) 7.40~7.60(5H, m) 7.94(1H, d, J=8 Hz)

EXAMPLE 13

(E)-3-{3-(2,5-Dimethylfuran-3-yl)-1H-pyrazol-4-yl}-N-{1-(3-methoxyphenyl)-2-(2-methylpyridin-6-yl)-ethyl}-2-propenamide

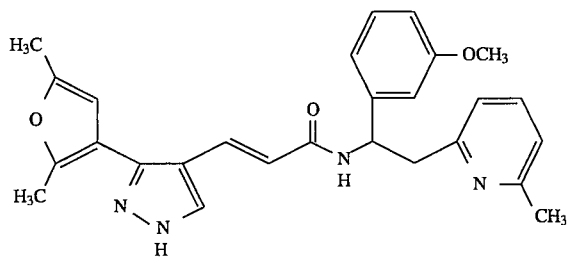

¹H-NMR (CDCl₃) δ (ppm) 2.23(3H, s) 2.24(3H, s) 2.51(3H, s) 3.13(1H, dd, J=8 Hz, 14 Hz) 3.28(1H, dd, J=5 Hz, 14 Hz) 3.73(3H, s) 5.39(1H, m) 6.01(1H, d, J=2 Hz) 6.23(1H, d, J=16 Hz) 6.72(1H, dd, J=3 Hz, 8 Hz) 6.78(1H, t, J=2 Hz) 6.83(1H, d, J=8 Hz) 6.88(1H, d, J=8 Hz) 7.00(1H, d, J=8 Hz) 7.17(1H, t, J=8 Hz) 7.41(1H, d, J=16 Hz) 7.46(1H, t, J=8 Hz) 7.80(1H, s) 8.04(1H, d, J=7 Hz)

EXAMPLE 14

(E)-N-{1-(3-Chlorophenyl)-2-(1-triphenylmethyl-imidazol-2-yl)}ethyl-3-{3-(2-chlorothiophen-5-yl)-1H-pyrazol-4-yl}-2-propenamide

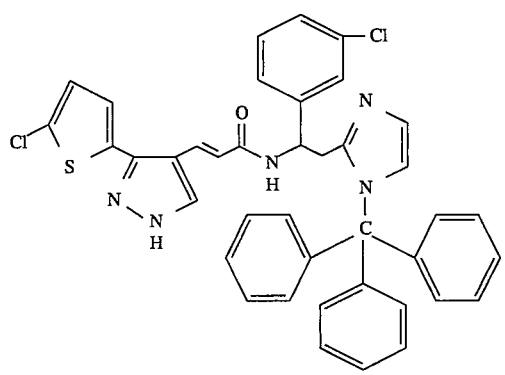

¹H-NMR (CDCl₃) δ (ppm) 2.32(1H, dd, J=4 Hz, 16 Hz) 2.68 (1H, dd, J=8 Hz, 16 Hz) 4.32~4.40(1H, m) 6.10(1H, d, J=16 Hz) 6.73(1H, s) 6.80(1H, d, J=4 Hz) 6.88~7.14 (11H, m) 7.25~7.35(9H, m) 7.53(1H, d, J=15 Hz) 7.67(1H, s) 8.82(1H, d, J=8 Hz)

EXAMPLE 15

(E)-N-(1,2-Diphenylethyl)-(4-phenyl-1H-imidazol-5-yl)-2-propenamide

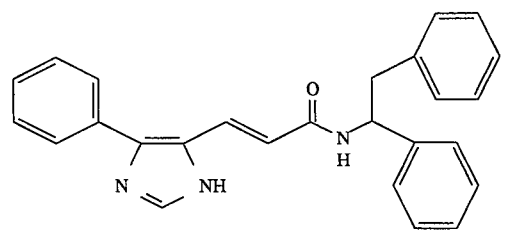

¹H-NMR (CDCl₃) δ (ppm) 3.04 (2H, d, J=8 Hz) 5.28 (1H, dd, J=7 Hz, 15 Hz) 6.40(1H, br-s) 6.98~7.30(16H, m) 7.56(1H, d, J=15 Hz)

EXAMPLE 16

(Z)-N-(1,2-Diphenylethyl)-(4-phenyl-1H-imidazol-5-yl)-2-propenamide

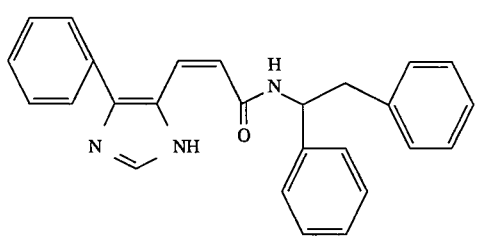

¹H-NMR (CDCl₃) δ (ppm) 3.15(2H, d, J=8 Hz) 5.32(1H, dd, J=8 Hz, 15 Hz) 5.51(1H, d, J=13 Hz) 6.46(1H, d, J=8 Hz) 6.82 (1H, d, J=13 Hz) 7.07~7.61(16H, br-s)

EXAMPLE 17

(E)-N-{1-(3-Chlorophenyl)-2-(1H-imidazol-2-yl)}-ethyl-3-[{3-(2-chlorothiophen-5-yl)}1H-pyrazol-4-yl}-2-propenamide

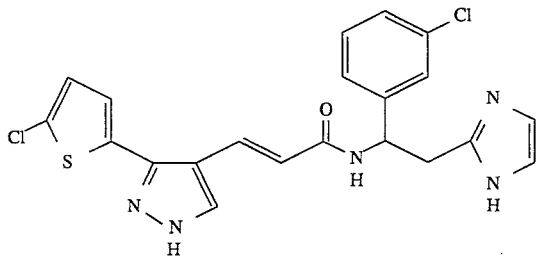

Trifluoroacetic acid (0.5 ml) was added to 10 ml of a dichloromethane solution of 0.25 g of the (E)-N-{1-(3-chlorophenyl)-2-(1-triphenylmethyl-imidazol-2-yl)}ethyl-3-{3-(2-chlorothiophen-5-yl)-1H-pyrazol-4-yl}-2-propenamide prepared in the Example 14 and the obtained mixture was stirred at room temperature overnight.

Trifluoroacetic acid (0.5 ml) was added to the reaction mixture. The obtained mixture was stirred for 6 hours and distilled in a vacuum to remove most of the trifluoroacetic acid. The residue was subjected to silica gel column chromatography and then to gradient elution with a dichloromethane/methanol (80:1 to 70:1 (v/v)) mixture to give 0.126 g of the title compound.

¹H-NMR (DMSO-d₆) δ (ppm) 3.05~3.16(2H, m) 5.37(1H, q, J=8 Hz) 6.47(1H, d, J=16 Hz) 6.91(2H, s) 7.15~7.34(6H, m) 7.44(1H, d, J=16 Hz) 8.21(1H, br-s) 8.80(1H, d, J=8 Hz) 13.4(1H, br-s)

EXAMPLE 18

(E)-3-{(2-Chlorothiophen-5-yl)-1H-pyrazol-4-yl}-N²-phenyl-N²-banzyl-2-propenohydrazide

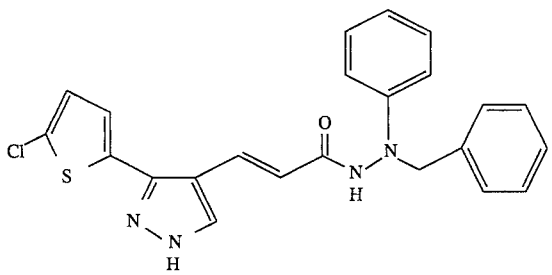

1.0 g of (E)-3-{3-(2-chlorothiophen-5-yl)-1H-pyrazol-4-yl}propenoic acid was dissolved in dichloromethane, followed by the addition thereto of 1.4 ml of oxalyl chloride and a catalytic amount of dimethylformamide. The obtained mixture was stirred at room temperature for 5 hours and distilled in a vacuum to remove the solvent and excess oxalyl chloride. The residue was dissolved in tetrahydrofuran, followed by the addition thereto of 1.6 ml of triethylamine and 940 mg of 1-phenyl-1-benzylhydrazine. The obtained mixture was stirred at room temperature for 30 minutes, followed by the addition thereto of water. The resulting mixture was extracted with ethyl acetate and the organic phase was dried over magnesium sulfate and distilled in a vacuum to remove the solvent. The residue was purified by silica gel column chromatography to give 620 mg of the title compound as a pale-yellow amorphous substance.

¹H-NMR (DMSO-d₆) δ (ppm) 4.72(2H, s) 6.46(1H, d, J=16 Hz) 6.70~6.81(3H, m) 7.10~7.48(10H, m) 7.54(1H, d, J=16 Hz)

EXAMPLE 19

(+)-(E)-N-{1-(3-Chlorophenyl)-2-(Pyridin-2-yl)-ethyl}-3-(1-cyanomethyl-3-phenylpyrazol-4-yl)-2-propenamide

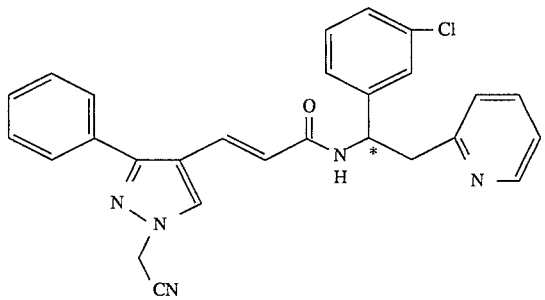

19.1 g of (−)-(E)-N-{1-(3-chlorophenyl)-2-(pyridin-2-yl)ethyl}-3-(3-phenyl-1H-pyrazol-4-yl)-2-propenamide was dissolved in 150 ml of dimethylformamide, followed by the addition thereto of 2.73 g of 60% sodium hydride in portions under cooling with ice and stirring. The obtained mixture was stirred for 45 minutes, followed by the dropwise addition thereto of 4.76 ml of bromoacetonitrile. After 30 minutes, ice-water was added to the resulting mixture, followed by the extraction with ethyl acetate. The organic phase was dried over magnesium sulfate and the magnesium sulfate was filtered out. The filtrate was distilled in a vacuum to remove the solvent and the residue was purified by silica gel chromatography (with an ethyl acetate/n-hexane system). The first eluate was (+)-(E)-N-{1-(3-chlorophenyl)-2-(pyridin-2-yl)ethyl}-3-(2-cyanomethyl-3-phenylpyrazol-4-yl)-2-propenamide, which was crystallized from ethyl acetate/diethyl ether to give 3.34 g of a pale-yellow solid. The second eluate was the title compound, which was crystallized from ethanol/isopropyl ether to give 11.7 g of a white crystal.

$[\alpha]_D^{20}=+44.5°$

¹H-NMR (CDCl₃) δ (ppm) 3.13(1H, dd, J=7 Hz, 14 Hz) 3.33(1H, dd, J=5 Hz, 14 Hz) 5.13(2H, s) 5.38(1H, m) 6.27(1H, d, J=16 Hz) 6.95(1H, d, J=8 Hz) 7.06(1H, m) 7.12~7.20(4H, m ) 7.37~7.46 (3H, m ) 7.30~7.60 (4H, m) 7.86(1H, s) 8.01(1H, d, J=7 Hz) 8.50(1H, d, J=5 Hz)

EXAMPLES 20 TO 26

The following compounds were each prepared in a similar manner to that of the Example 19.

EXAMPLE 20

(+)-(E)-3-(1-Cyanomethyl-3-phenylpyrazol-4-yl)-N-{1-(2,5-difluorophenyl)-2-(pyridin-2-yl)ethyl-2-propenamide

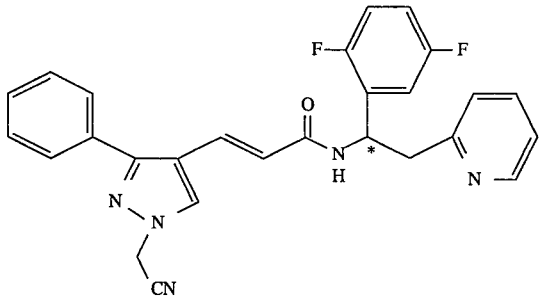

m.p.: 175°~176° C.

MS m/z: 470 (MH$^+$)

elemental analysis (as $C_{27}H_{21}F_2N_5O$) calcd.: C 69.08 H 4.51 N 14.92%.

found: C 69.10 H 4.56 N 14.88%

$[\alpha]_D^{20}$=+20.3°

$^1$H-NMR (CDCl$_3$) δ (ppm) 3.19(1H, dd, J=7 Hz, 14 Hz) 3.33(1H, dd, J=5 Hz, 14 Hz) 5.12(2H, s) 5.63(1H, dd, J=5 Hz, 7 Hz) 6.29 (1H, d, J=16 Hz) 6.63~6.67(1H, m) 6.79~6.85(1H, m) 6.94~7.00(2H, m) 7.15(ddd, J=1 Hz, 5 Hz, 5 Hz) 7.36~7.58(6H, m) 7.87(1H, s) 8.05(1H, d, J=7 Hz) 8.49(1H, ddd, J=1 Hz, 2 Hz, 5 Hz)

EXAMPLE 21

(+)-(E)-N-{1-(2-Chloropyridin-6-yl)-2-(pyridin-2-yl)-ethyl}-3-{1-cyanomethyl-3-(3-fluorophenyl)pyrazol-4-yl}-2-propenamide

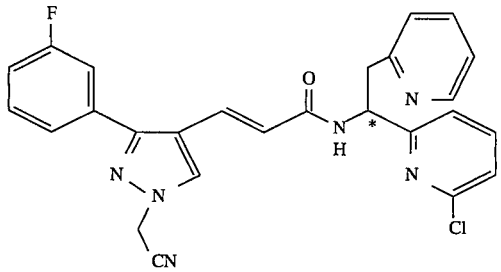

$[\alpha]_D^{20}$=+75.3°

$^1$H-NMR (CDCl$_3$) δ (ppm) 3.31(1H, dd, J=6 Hz, 14 Hz) 3.43(1H, dd, J=7 Hz, 14 Hz) 5.13(2H, s) 5.51(1H, dd, J=7 Hz, 13 Hz) 6.30(1H, d, J=16 Hz) 7.00~7.16(5H, m) 7.26~7.56(6H, m) 7.71(1H, d, J=7 Hz) 7.86(1H, s) 8.47(1H, m)

EXAMPLE 22

(+)-(E)-N-{1-(4-Chloropyridin-2-yl)-2-(pyridin-2-yl)-ethyl-3-(1-cyanomethyl)-3-phenylpyrazol-4-yl)}-2-propenamide

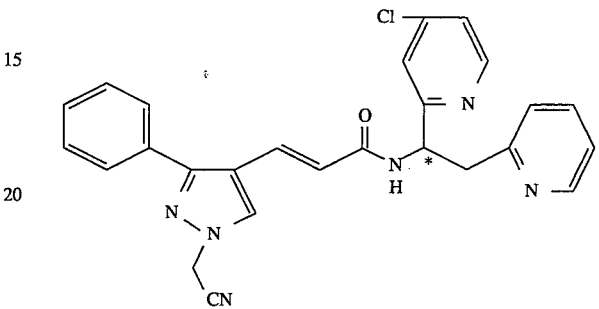

$^1$H-NMR (CDCl$_3$) δ (ppm) 3.33 (1H, dd, J=5 Hz, 14 Hz) 3.43(1H, dd, J=7 Hz, 14 Hz) 5.12(2H, s) 5.51 (1H, dd, J=5 Hz, 7 Hz) 6.30 (1H, d, J=16 Hz) 7.03(1H, d, J=7 Hz) 7.10~7.15(3H, m) 7.40~7.59(6H, m) 7.84(1H, d, J=7 Hz) 7.86(1H, s) 7.84(1H, d, J=7 Hz) 7.86(1H, s) 8.41(1H, d, J=5 Hz) 8.47 (1H, ddd, J=1 Hz, 2 Hz, 5 Hz)

EXAMPLE 23

(E)-3-{1-Cyanomethyl-3-(2,5-dimethylfuran-3-yl)-pyrazol-4-yl}N-{1-(3-methoxyphenyl)-2-(2-methyl-pyridin-6-yl)ethyl}-2-propenamide

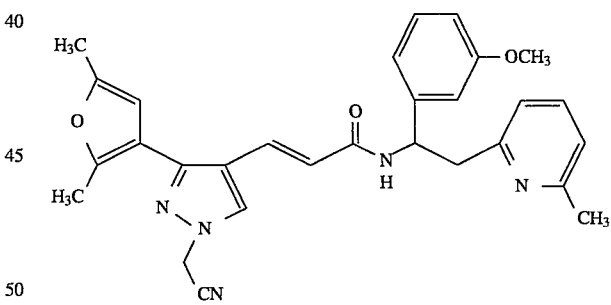

$^1$H-NMR (CDCl$_3$) δ (ppm) 2.26(3H, s) 2.29(3H, s) 2.53(3H, s) 3.11(1H, dd, J=8 Hz, 14 Hz) 3.29(1H, dd, J=4 Hz, 14 Hz) 3.73(3H, s) 5.35(1H, m) 6.06(1H, s) 6.18(1H, d, J=16 Hz) 6.70~6.74(2H, m) 6.77~6.82(2H, m) 7.00(1H, d, J=8 Hz) 7.16(1H, m) 7.42(1H, d, J=16 Hz) 7.43(1H, t, J=8 Hz) 7.74(1H, s) 7.94(1H, d, J=7 Hz)

EXAMPLE 24

(E)-3-{1-Cyanomethyl-3-(2,5-dimethylfuran-3-yl)-pyrazol-4-yl}N-{1-(3-methoxyphenyl)-2-(Pyridin-2-yl)}ethyl-2-propenamide

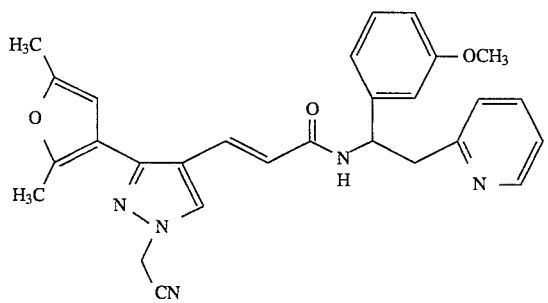

$^1$H-NMR (CDCl$_3$) δ (ppm) 2.27(3H, s) 2.30(3H, s) 3.17(1H, dd, J=8 Hz, 14 Hz) 3.33 (1H, dd, J=5 Hz, 14 Hz) 3.72(3H, s) 5.05(2H, s) 5.39(1H, m) 6.06(1H, s) 6.20(1H, d, J=16 Hz) 6.70~6.76(2H, m) 6.79(1H, d, J=8 Hz) 7.00(1H, d, J=8 Hz) 7.12~7.20(2H, m) 7.40(1H, d, J=16 Hz) 7.55(1H, td, J=2 Hz, 8 Hz) 7.76(1H, s) 7.78(1H, d, J=8 Hz) 8.51(1H, d, J=5 Hz)

EXAMPLE 25

(E)-(1-Cyanomethyl-3-(2,5-dimethylfuran-3-yl)-pyrazol-4-yl)-N-{1-(2-methylpyridin-6-yl)-2-(pyridin-2-yl)}ethyl-2-propenamide

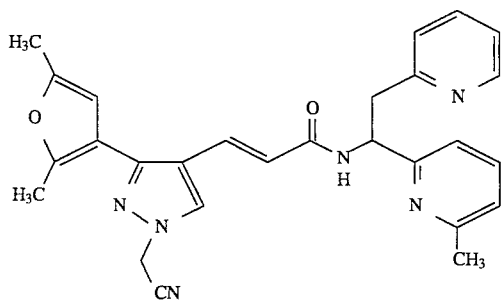

$^1$H-NMR (CDCl$_3$) δ (ppm) 2.27(3H, s) 2.31(3H, s) 2.52(3H, s) 3.28(1H, dd, J=6 Hz, 14 Hz) 3.42(1H, dd, J=7 Hz, 14 Hz) 5.08(2H, s) 5.49(1H, dd, J=7 Hz, 14 Hz) 6.07(1H, s) 6.25(1H, d, J=16 Hz) 6.81(1H, d, J=8 Hz) 6.83(1H, d, J=8 Hz) 7.05(1H, d, J=8 Hz) 7.11(1H, m) 7.40(1H, m) 7.42(1H, d, J=16 Hz) 7.53(1H, td, J=2 Hz, 8 Hz) 7.67(1H, d, J=7 Hz) 7.79(1H, s) 8.48(1H, m)

EXAMPLE 26

(+)-(E)-N-{1-(3-Chlorophenyl)-2-(pyridin-2-yl)}-ethyl-3-{1-cyanomethyl-3-(2-chlorothiophen-5-yl)-pyrazol-4-yl}-2-propenamide

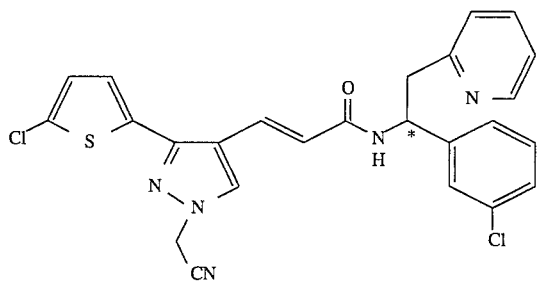

[α]$_D^{20}$=+54.9°

$^1$H-NMR (CDCl$_3$) δ (ppm) 3.14(1H, dd, J=7 Hz, 14 Hz) 3.35(1H, dd, J=5 Hz, 14 Hz) 5.08(2H, s) 5.39(1H, m) 6.32(1H, d, J=16 Hz) 6.88 (1H, d, J=4 Hz) 6.95 (1H, d, J=8 Hz) 7.05~7.20(6H, m) 7.54~7.60(2H, m) 7.82(1H, s) 8.13(1H, d, J=6 Hz) 8.55(1H, m)

EXAMPLE 27

(E)-3-{1-Cyanomethyl-3-(thiophen-2-yl)pyrazol-4-yl}-N-(1,2-diphenylethyl)-2-propenthioamide

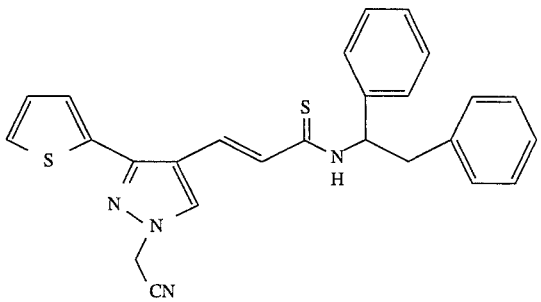

720 mg of (E)-3-{1-cyanomethyl-3-(thiophen-2-yl)-pyrazol-4-yl}-N-(1,2-diphenylethyl)-2-propenamide and 2.2 g of Lawson's reagent were suspended in toluene. The obtained suspension was refluxed for 40 minutes and brought to room temperature. The precipitated solid was filtered out and the filtrate was distilled in a vacuum to remove the solvent. The residue was purified by silica gel chromatography to give 180 mg of the title compound as a pale-yellow amorphous substance.

$^1$H-NMR (CDCl$_3$) δ (ppm) 3.25(1H, dd, J=7 Hz, 14 Hz) 3.42(1H, dd, J=6 Hz, 14 Hz) 6.04(1H, td, J=7 Hz, 7 Hz) 6.57(1H, d, J=16 Hz) 7.08~7.45(14H, m) 7.73(1H, s) 7.84(1H, d, J=16 Hz)

EXAMPLE 28

The compound of Example 2 is obtained alternatively in the following manner.

4.0 g of (−)-[1-(4-chloro-pyridin-2-yl)-2-(pyridin-2-yl)]-ethylamine of Preparation Example 32 was dissolved in tetrahydrofurane under nitrogen gas and then 4.2 g of (E)-[3-(3-fluorophenyl)-1H-pyrazol-4-yl]-2-propenoic acid and 3.6 g of 1-(3-dimethylaminopropyl)-3-ethylcarbodiimide hydrochloride were added to the solution. It was stirred at 24° C. for 19 hours. The reaction mixture was diluted with 120 ml of water and extracted with 240 ml of a 15% solution in methanol of ethyl acetate, and 40 ml of ethyl acetate. The two extract liquids were combined with each other and it was washed separately in order with 80 ml of a 1% aqueous acetic acid, 80 ml of a saturated solution of sodium hydrogencarbonate and 80 ml of a saturated salt water. It was concentrated and dried at a reduced pressure to obtain a crude product of the above titled compound having an HPLC purity of 98.1%. The product was dissolved in 120 ml of 1N hydrochloric acid, washed twice with 80 ml of dichloromethane and neutralized with sodium hydrogencarbonate. The precipitates were collected by filtration, washed well with water and dried in air at 50° C. for 5 hours to obtain 17.25 g of the above titled compound with 95% yield, having an HPLC purity of 98.6%, being powder in light yellow.

$[\alpha]_D^{20}$=+52.5° (c=0.594, methanol)

$^1$H-NMR (CDCl$_3$) δ (ppm) 3.34~3.46(2H, m) 5.55(1H, m) 6.30(1H, d, J=16 Hz) 7.04~7.20(5H, m) 7.20~7.30(2H, m) 7.38(1H, dr, J=6 Hz, 9 Hz) 7.56 (1H, d, J=16 Hz) 7.58(1H, dt, J=2 Hz, 8 Hz) 7.83 (1H, s ) 8.01 (1H, d, J=8 Hz) 8.41(1 Hz, d, J=5 Hz) 8.46(1H, d, J=5 Hz)

EXAMPLE 29

Monofumarate monohydrate of the compound of Example 2

38.0 g of the compound obtained by Example 2 was dissolved in 480 ml of ethanol and 160 ml of water, heated, and the insoluble was filtrated out. The liquid was stirred with ice and seeded. In 40 minutes, the precipitated crystals were collected by filtration and dried in air at 80° C. for 2 days to obtain 39.0 g of the titled monofumarate monohydrate having a melting point of 153.5°–156° C.

$[\alpha]_D$=+44.8° (c=1, methanol)

NMR (DMSO-α6, δ) 3.18 (1H, dd J=14 Hz, 9 Hz) 3.32 (1H, dd, J=14 Hz, 5 Hz) 5.43~5.50(1H, m) 6.44(1H, d, J=16 Hz) 6.63(2H, s) 7.17~7.35(6H, m) 7.40~7.44(2H, m) 7.52~7.59(1H, m) 7.66(1H, ddd, J=8 Hz, 8 Hz, 2 Hz) 8.07(1H, bs) 8.48(1H, ddd, J=5 Hz, 2 Hz, 1 Hz) 8.52(1H, dd, J=5 Hz, 1 Hz) 8.63(1H, d, J=8 Hz)

We claim:

1. A propenoic acid compound represented by the formula (I) or a pharmacologically acceptable salt thereof:

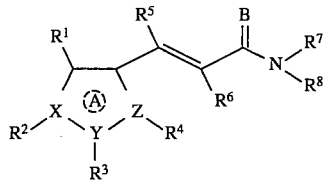

wherein A represents an aromatic ring;

two of X, Y and Z are nitrogen and the other is carbon;

$R^1$ represents optionally substituted aryl or optionally substituted heteroaryl;

$R^2$, $R^3$ and $R^4$ may be the same or different from each other and each represents hydrogen, lower alkyl, lower alkenyl, lower alkynyl or a group represented by formula —W-Q wherein W is a lower alkyl group, and Q represents optionally substituted aryl, optionally substituted heteroaryl, cycloalkyl, cyano, hydroxyl, lower alkoxy, acyloxy, carboxyl or a group represented by formula —NR$^9$R$^{10}$ wherein R$^9$ and R$^{10}$ may be the same or different from each other and each represents hydrogen, lower alkyl, acyl, carbamoyl or alkylcarbanoyl, or alternatively R$^9$ and R$^{10}$ may represent, together with the nitrogen atom to which they are bonded, a cyclic group;

$R^5$ and $R^6$ may be the same or different from each other and each represents hydrogen or lower alkyl;

B represents oxygen or sulfur; and $R^7$ and $R^8$ may be the same or different from each other and each represents hydrogen, lower alkyl, lower alkoxy, optionally substituted aryl, optionally substituted arylalkyl, optionally substituted heteroaryl, optionally substituted heteroarylalkyl, optionally protected carboxyalkyl, a group represented by the formula:

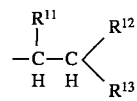

wherein $R^{11}$ represents hydrogen, lower alkyl, optionally substituted aryl, optionally substituted arylalkyl or optionally substituted heteroaryl; $R^{12}$ represents hydrogen, hydroxyl, lower alkyl, lower alkoxy, carbonyl, protected carboxyl, optionally substituted amino, optionally substituted aryl, optionally substituted heteroaryl, optionally substituted aryalkyl or optionally substituted heteroarylalkyl; and R$^{13}$ is represents hydrogen, hydroxyl, lower alkyl, lower alkoxy, optionally substituted aryl or optionally substituted heteroaryl, or a group represented by formula —V-E wherein V represents a group represented by formula —CO—, a group represented by formula —(CH$_2$)— or a group represented by the formula:

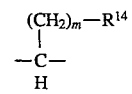

wherein $R^{14}$ represents optionally substituted aryl or optionally substituted heteroaryl; and m is an integer of 0 or 1; and E represents optionally substituted aryl or optionally substituted heteroaryl, or alternatively, $R^7$ and $R^8$ may represent, together with the nitrogen atom to which they are bonded, a cyclic group which may be substituted.

2. The propenoic acid compound or a pharmocologically acceptable salt thereof as set forth in claim 1, which is represented by the formula:

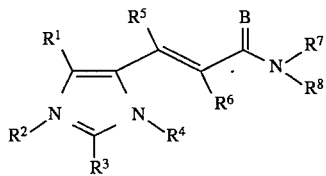

wherein $R^1$, $R^3$, $R^4$, $R^5$, $R^6$, $R^7$, $R^8$ and B are each as defined in claim 1.

3. The propenoic acid compound or a pharmacologically acceptable salt thereof as set forth in claim 1 which is represented by the formula:

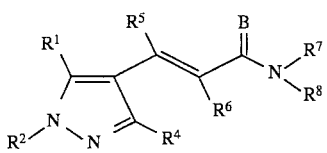

wherein $R^1, R^2, R^4, R^5, R^6, R^7, R^8$ and B are each as defined in claim 1.

4. The propenoic acid compound or a pharmacologically acceptable salt thereof as set forth in claim 1 which is represented by the formula:

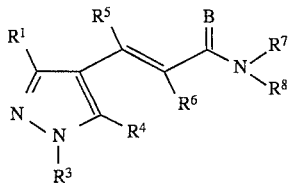

wherein $R^1, R^3, R^4, R^5, R^6, R^7, R^8$ and B are each as defined in claim 1.

5. A method of treating a disease against which adenosine antagonism is efficacious, comprising administering a pharmacologically effective amount of a compound as defined in claim 1 or a pharmacologically acceptable salt thereof to a subject who suffers or will suffer from the disease.

6. The method as in claim 5, in which the adenosine antagonism is adenosine A1 receptor antagonism.

7. The method as in claim 5 in which the disease is renal failure.

* * * * *